United States Patent
Oezbek et al.

(10) Patent No.: US 11,589,927 B2
(45) Date of Patent: Feb. 28, 2023

(54) SURGICAL NAVIGATION SYSTEM AND METHOD

(71) Applicant: Stryker European Operations Limited, Carrigtwohill (IE)

(72) Inventors: Christopher Oezbek, Berlin (DE); Christian Winne, Berlin (DE); Bartosz Kosmecki, Berlin (DE)

(73) Assignee: Stryker European Operations Limited, Carrigtwohill (IE)

( * ) Notice: Subject to any disclaimer, the term of this patent is extended or adjusted under 35 U.S.C. 154(b) by 507 days.

(21) Appl. No.: 16/610,132

(22) PCT Filed: May 4, 2018

(86) PCT No.: PCT/IB2018/053130
§ 371 (c)(1),
(2) Date: Nov. 1, 2019

(87) PCT Pub. No.: WO2018/203304
PCT Pub. Date: Nov. 8, 2018

(65) Prior Publication Data
US 2020/0085511 A1    Mar. 19, 2020

(30) Foreign Application Priority Data

May 5, 2017  (EP) .................................... 17169700

(51) Int. Cl.
*A61B 34/20*    (2016.01)
*A61B 34/10*    (2016.01)
(Continued)

(52) U.S. Cl.
CPC .............. *A61B 34/20* (2016.02); *A61B 34/10* (2016.02); *A61B 90/39* (2016.02); *H04N 13/344* (2018.05);
(Continued)

(58) Field of Classification Search
CPC ................................ A61B 34/10; A61B 34/20
See application file for complete search history.

(56) References Cited

U.S. PATENT DOCUMENTS 5,638,819 A    6/1997  Manwaring et al.
7,660,623 B2   2/2010  Hunter et al.
(Continued)

FOREIGN PATENT DOCUMENTS

AU    2002230901 B2   9/2006
CN       106109015 A  11/2016
(Continued)

OTHER PUBLICATIONS

International Search Report for Application No. PCT/IB2018/053130 dated Aug. 14, 2018, 5 pages.
(Continued)

*Primary Examiner* — Olivia C Chang
(74) *Attorney, Agent, or Firm* — Howard & Howard Attorneys PLLC

(57) ABSTRACT

The present disclosure relates to a surgical navigation system for the alignment of a surgical instrument and methods for its use, wherein the surgical navigation system may comprise a head-mounted display comprising a lens. The surgical navigation system may further comprise tracking unit, herein the tracking unit may be configured to track a patient tracker and/or a surgical instrument. Patient data may be registered to the patient tracker. The surgical instrument may define an instrument axis. The surgical navigation system may be configured to plan one or more trajectories based on the patient data. The head-mounted display may be configured to display augmented reality visualization, including an augmented reality position alignment visual- (Continued)

ization and/or an augmented reality angular alignment visualization related to the surgical instrument on the lens of the head-mounted display.

21 Claims, 9 Drawing Sheets

(51) Int. Cl.
*A61B 90/00* (2016.01)
*H04N 13/344* (2018.01)

(52) U.S. Cl.
CPC . *A61B 2034/107* (2016.02); *A61B 2034/2055* (2016.02); *A61B 2090/363* (2016.02); *A61B 2090/365* (2016.02); *A61B 2090/368* (2016.02); *A61B 2090/3983* (2016.02)

(56) References Cited

U.S. PATENT DOCUMENTS

| | | |
|---|---|---|
| 9,119,670 B2 | 9/2015 | Yang et al. |
| 9,629,523 B2 | 4/2017 | Tesar et al. |
| 9,645,785 B1 | 5/2017 | Hannaford et al. |
| 9,681,796 B2 | 6/2017 | Tesar et al. |
| 9,861,446 B2 | 1/2018 | Lang |
| 9,867,721 B2 | 1/2018 | Hunter |
| 2002/0082498 A1 | 6/2002 | Wendt et al. |
| 2005/0203384 A1 | 9/2005 | Sati et al. |
| 2008/0154120 A1 | 6/2008 | von Jako et al. |
| 2013/0060146 A1 | 3/2013 | Yang et al. |
| 2017/0027651 A1 | 2/2017 | Esterberg |
| 2017/0099479 A1 | 4/2017 | Browd et al. |
| 2017/0258526 A1 | 9/2017 | Lang |
| 2017/0367771 A1 | 12/2017 | Tako et al. |
| 2018/0153709 A1 | 6/2018 | Hunter |

FOREIGN PATENT DOCUMENTS

| | | |
|---|---|---|
| EP | 1103229 A2 | 5/2001 |
| EP | 1844726 A2 | 10/2007 |
| JP | 2014524753 A | 9/2014 |
| WO | 2010067267 A1 | 6/2010 |
| WO | 2016154557 A1 | 9/2016 |
| WO | 2016207628 A1 | 12/2016 |
| WO | 2017015738 A1 | 2/2017 |
| WO | 2017160651 A1 | 9/2017 |
| WO | 2018022523 A1 | 2/2018 |

OTHER PUBLICATIONS

English language abstract for JP 2014-524753 A extracted from espacenet.com database on Oct. 29, 2022, 2 pages.
English language abstract and machine-assissted English translation for CN 106109015 A extracted from espacenet.com database on Jan. 11, 2023, 10 pages.

SURGICAL NAVIGATION SYSTEM AND METHOD

RELATED APPLICATIONS

This application is a national stage of International Application No. PCT/IB2018/053130, filed on May 4, 2018, which claims priority to and the benefit of European Patent Application No. 17169700.6, filed on May 5, 2017, the entire contents of both of which are hereby incorporated by reference in their entirety.

TECHNICAL FIELD

The present disclosure relates generally to a surgical navigation system for supporting surgical interventions. More specifically, but not exclusively, the present disclosure relates generally to a holographic surgical navigation system.

BACKGROUND

Computer-assisted surgery, including surgical navigation systems, is a growing trend in the medical field. The surgical navigation system, in combination with pre-operative images and/or patient data may be utilized during a surgical intervention to support the surgeon in executing a medical procedure. For that purpose, image guidance surgical navigation systems are used for open and minimally-invasive surgical interventions, such as spine, joint, and/or neuro surgery. The aim of such surgical navigation systems is to determine the position of a surgical instrument used by the surgeon that can be illustrated or visualized in the pre-operative images and/or patient data corresponding to the patient's anatomy. Continuous detection of the position and/or orientation (i.e., pose) of the patient and/or the surgical instrument (so-called navigation data) are necessary to provide an accurate spatial representation of the surgical instrument relative to the patient.

The surgical navigation system may also visualize the position and/or alignment of a medical device or implant to the surgeon, such as the position and alignment of a pedicle screw for multiple vertebra fixation in the context of spine surgery. During operation, the surgical navigation system may provide a visualization to the surgeon, allowing the surgeon to see an overlay of the position of the surgical instrument and/or the medical device/implant projected exactly on an image or visualization of the patient.

Taking existing solutions into account, it is to be noted that known surgical navigation solutions do not sufficiently address the surgical navigation system guidance and alignment of surgical instruments. A further disadvantage of existing solutions is that the visualization is detached from the surgical site, forcing a deviation of attention of the surgeon.

Thus, there is a need for new surgical navigation systems addressing these disadvantages.

SUMMARY

In an exemplary configuration of a surgical navigation system and method of aligning a surgical instrument, the surgical navigation system may be configured to provide an augmented reality visualization during a medical intervention. Generally, the surgical navigation system may comprise a tracking unit. The tracking unit may comprise one or more position sensors. The surgical navigation system may further comprise a head-mounted display, patient tracker, and a surgical instrument, each of which may comprise one or more tracking members or makers configured to be detected by the one or more position sensors of the tracking unit. The tracking unit may be configured to continuously track the position and/or orientation (pose) of the head-mounted display, patient tracker, and surgical instrument within a localized or common coordinate system. The surgical navigation system may be further configured to register the position and/or orientation of the head-mounted display, patient tracker, and surgical instrument with patient data to generate and display an augmented reality visualization on a lens or screen of the head-mounted display. The augmented reality visualization may comprise the surgical instrument and/or a target trajectory axis overlaid on patient data, wherein the patient data may comprise pre-operative images of the patient's anatomy and/or or target objects. The target object(s) may comprise the planned surgical pathway, a planned position for an implant or medical device, and/or an anatomical feature of the patient.

The augmented reality visualization may comprise a position alignment visualization and/or an angular alignment visualization. The navigation system may be configured to display the position alignment visualization and/or the angular alignment visualization on the head-mounted display such that the visualizations are overlaid on the actual patient from the perspective of the surgeon to create a 3-D or holographic visualization.

In another example configuration of an augmented reality system, the augmented reality system may comprise a surgical navigation system, a patient tracker trackable by said surgical navigation system, and a surgical instrument trackable by said surgical navigation system. The augmented reality system may further comprise a head-mounted display comprising a lens and a controller configured to display an augmented reality position alignment visualization as two axis-aligned deviation vectors comprising a decomposition of a distance vector from a target point on a target trajectory axis to the surgical instrument on said lens.

In yet another example configuration of an augmented reality system, the augmented reality system may comprise a head-mounted display including a lens. The augmented reality system may also comprise a surgical navigation system comprising a tracking unit configured to track a number of objects positioned within a defined field or coordinate system, such as a surgical field. The augmented reality system may also include a patient tracker registered to patient data and trackable by said surgical navigation system, and a surgical instrument having an instrument tracker trackable by said surgical navigation system. The instrument tracker may be configured to define an instrument axis of the surgical instrument. The augmented reality system may also comprise a controller configured to generate an augmented reality position alignment visualization as two axis-aligned deviation vectors comprising the decomposition of a distance vector from a target point on a target trajectory axis to a point on the surgical instrument to display on said lens of said head-mounted display.

In yet another example configuration of an augmented reality system, a surgical navigation system may include a patient tracker and a surgical instrument tracker. The surgical navigation system may be configured to plan a target trajectory axis based on patient data and for the alignment of a tip of a surgical instrument with the target trajectory axis. The surgical navigation system may further comprise a head-mounted display comprising a head-mounted display tracker, wherein the head-mounted display is configured to display an augmented reality position alignment visualization comprising two axis-aligned deviation vectors comprising the decomposition of a distance vector from a point on the target trajectory axis to the tip of the surgical instrument. The head-mounted display may further be configured to display an augmented reality angular alignment visualization comprising a deviation angle which represents the angle between a first direction vector of the instrument axis and a second direction vector of the target trajectory axis.

An exemplary method of displaying surgical navigation information may comprise a head-mounted display with a surgical navigation system including a surgical instrument having a tip in view of a surgical plan including a target trajectory axis. The method may comprise the step of displaying an augmented reality position alignment visualization comprising two axis-aligned deviation vectors on a head-mounted display, said two-axis aligned deviation vectors comprising a first vector and a second vector wherein the first vector and second vector are representative of the decomposition of a distance vector from a point on the target trajectory axis to the tip of the surgical instrument. The method may further comprise the step of updating the augmented reality position alignment visualization displayed on the head-mounted display to indicate a relative location of the surgical instrument to the target trajectory axis from the perspective of the head-mounted display.

Another exemplary method of aligning a surgical instrument may comprise a surgical navigation system, wherein the surgical navigation system includes a tracking unit configured to track the position of a head-mounted display, a patient tracker, and a surgical instrument tracker. The surgical navigation system may further be configured to plan a target trajectory axis based on patient data registered to the patient tracker. The method of aligning the surgical instrument may comprise the step of displaying on the head-mounted display an augmented reality position alignment visualization as two axis-aligned deviation vectors comprising the decomposition of a distance vector from a point on the target trajectory axis to a tip of the surgical instrument. The method may further comprise the step of displaying on the head-mounted display an augmented reality angular alignment visualization comprising a deviation angle which shows the angle between a first direction vector of the axis of the surgical instrument and a second direction vector of the target trajectory axis. The method may further comprise the step of continuously updating the augmented reality position alignment visualization and/or the augmented reality angular alignment visualization displayed on the head-mounted display based on the tracking unit to indicate the relative location of the surgical instrument to the target trajectory axis from the perspectives of the head-mounted display.

It is an advantage of the proposed apparatus and method to make medical interventions more effective, safer, and more precise.

BRIEF DESCRIPTION OF THE DRAWINGS

Advantages of the present disclosure will be readily appreciated as the same becomes better understood by reference to the following detailed description when considered in connection with the accompanying drawings wherein.

DETAILED DESCRIPTION

Figure 1A:
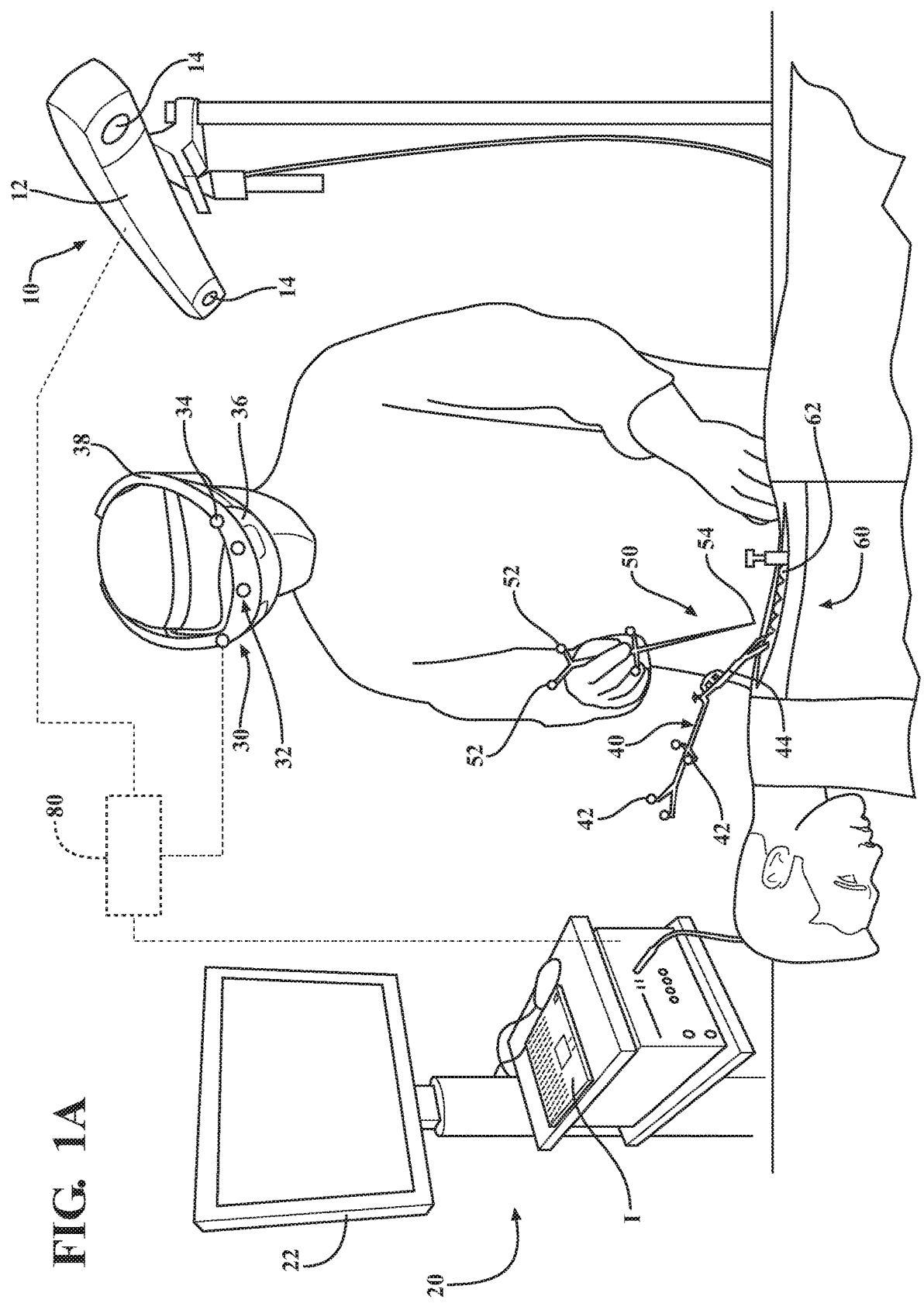
FIG. 1A is a perspective view of a surgeon using a first configuration of a surgical navigation system including a head-mounted display and a surgical tracking unit.
Figure 1B:
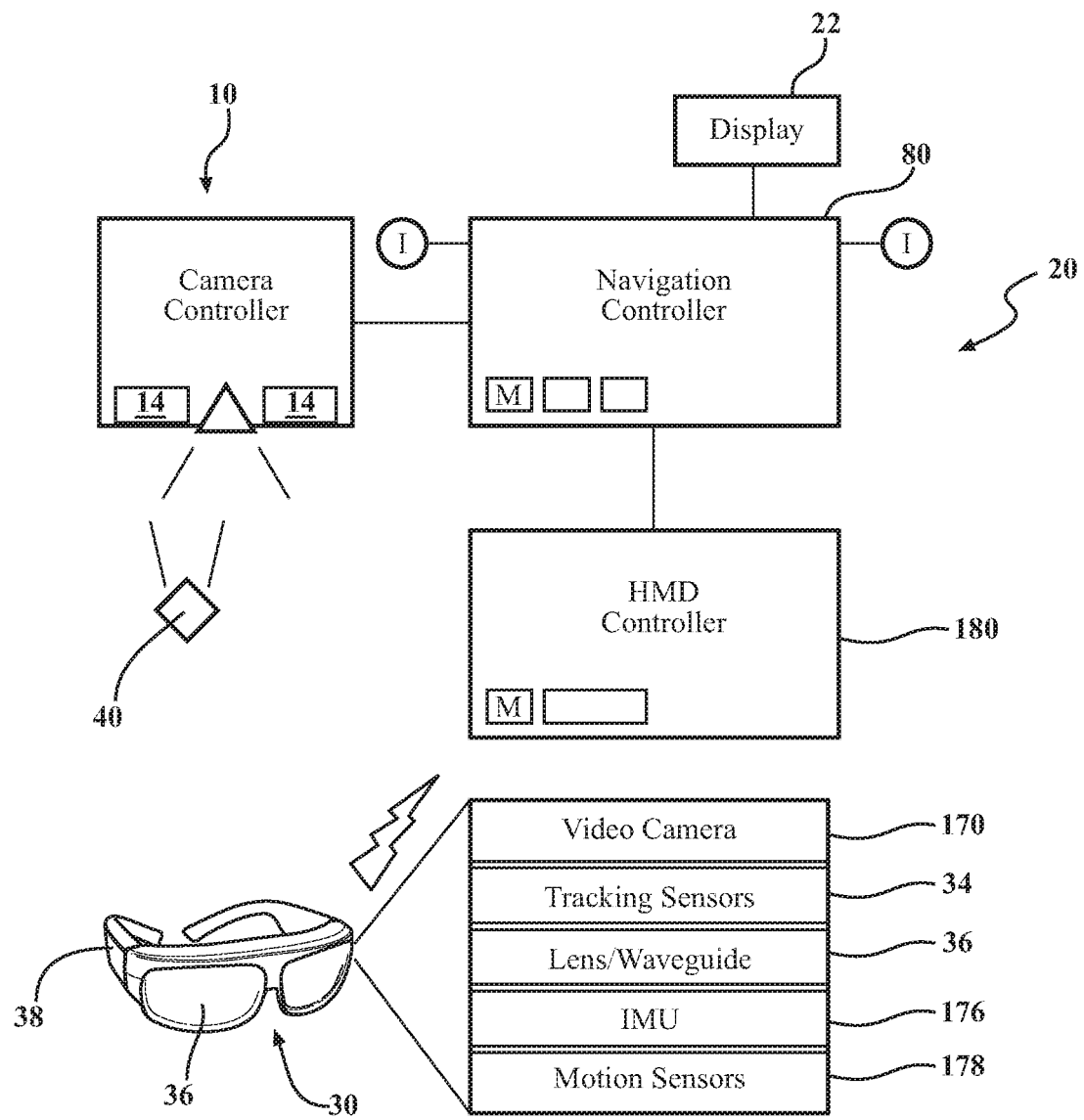
FIG. 1B is a schematic view of a control system for the surgical navigation system of FIG. 1A.

FIGS. 1A and 1B illustrate an exemplary configuration of a surgical navigation system 20, which may include a tracking unit 10 and a head-mounted display 30. The surgical navigation system 20 may be utilized by a surgeon to assist the surgeon in executing a medical procedure, such as inserting a pedicle screw as part of a multiple vertebrae fixation or removing a brain tumor.

The surgical navigation system 20 may comprise a navigation interface that includes one or more user inputs I and one or more displays 22. The user input I may be configured to allow the surgeon to input or enter patient data. The patient data may comprise patient images, such as pre-operative images of the patient's anatomy. These images may be based on MRI scans, radiological scans or computed tomography (CT) scans of the patient's anatomy. The patient data may also include additional information related to the type of medical procedure being performed, the patient's anatomical features, the patient's specific medical condition, and/or operating settings for the surgical navigation settings. For example, in performing a spinal surgery, the surgeon may enter information via the user input I related to the specific vertebrae the medical procedure is being performed on. The surgeon may also input various anatomical dimension related to the vertebrae and/or the size and shape of a medical device or implant to be inserted during the medical procedure.

The display 22 of the surgical navigation system 20 may be configured to display various prompts or data entry boxes. For example, the display 22 may be configured to display a text box or prompt that allows the surgeon to manually enter or select the type of surgical procedure to be performed. The display 22 may also be configured to display patient data, such as a pre-operative image or scan. As described above, the pre-operative image may be based on MRI scans, radiological scans or computed tomography (CT) scans of the patient's anatomy. The pre-operative image may be uploaded to the surgical navigation system and displayed on the display 22. The display 22 may be further configured to display a surgical plan for a medical procedure overlaid on the patient data or image. The surgical plan may include a surgical pathway for executing a medical procedure or a planned trajectory or orientation for the medical instrument during the medical procedure. The surgical plan may also include overlaying the position and/or orientation of an implant or medical device to be inserted during the medical procedure on the patient data or image.

The surgical navigation system 20 may further comprise a navigation controller 80. The navigation controller 80 can be a personal computer or laptop computer. The navigation controller 80 may be in communication with the user input I, display 22, central processing unit (CPU) and/or other processors, memory (not shown), and storage (not shown). The navigation controller 80 may further comprise software and/or operating instructions related to the operation of the surgical navigation system 20. The software and/or operating instructions may comprise planning system configured to find an accurate position and/or angular alignment of the surgical instrument 50 in relation to the patient 60. The navigation controller 80 may be in wired or wireless communication with the head-mounted display. Accordingly, the head-mounted display 30 may include a wireless or wired transceiver.

The surgical navigation system 20 may further comprise a tracking unit 10. The tracking unit 10 may also be referred to as a tracking system or camera unit. The tracking unit 10 may comprise a housing 12 comprising an outer casing that houses one or more position sensors 14. The position sensors may comprise cameras, such as charge-coupled devices (CCD) cameras, CMOS cameras, and/or optical image cameras, electromagnetic sensors, magnetoresistance sensors, radio frequency sensors, or any other sensor adapted to sufficiently sense the position of a navigation marker. In some configurations, at least two position sensors 14 may be employed, preferably three or four. For example, the position sensors 14 may be separate CCDs. In one configuration three, one-dimensional CCDs are employed. Two-dimensional or three-dimensional sensors could also be employed. It should be appreciated that in other configurations, separate tracking units 10, each with a separate CCD, or two or more CCDs, could also be arranged around the operating room. The CCDs detect light signals, such as infrared (IR) signals.

The housing 12 of the tracking unit 10 may be mounted on an adjustable stand or arm to allow for repositioning of the position sensor(s) 14. For example, the adjustable stand or arm may be configured to allow for repositioning of the position sensor(s) 14 to provide an optimal view of the surgical field that ideally is free from obstructions.

The tracking unit 10 may include a sensor controller (not shown) in communication with the position sensors 14, such as optical sensors 14, and configured to receive signals from the optical sensors 14. The sensor controller may communicate with the navigation controller 80 through either a wired and/or wireless connection. One such connection may be the RS-232 communication standard or the IEEE 1394 interface, which are serial bus interface standards for high-speed communications and isochronous real-time data transfer. The connection could also use a company-specific protocol or network protocols such as UDP or TCP. In other embodiments, the optical sensors 14 may be configured to communicate directly with the navigation controller 80.

The tracking unit 10 in communication with the surgical navigation system 20 via the navigation controller 80 may be used to determine the relative position of the head-mounted display 30, a surgical instrument 50, and a patient 60 or region of interest 62. Utilizing the relative position of the head-mounted display 30, the one or more surgical instruments 50, and the patient 60, the navigation controller 80 of the surgical navigation system 20 is thus able to compute augmented reality (AR) visualizations that may be displayed in the head-mounted display 30 in registration with the patient 60 and the head-mounted display 30.

The surgical instrument 50 may comprise one or more instrument markers 52 configured to be detectable by the position sensors 14 of the tracking unit 10. The surgical instrument 50 may be configured to comprise passive tracking elements or instrument markers 52 (e.g., reflectors) for transmitting light signals (e.g., reflecting light emitted from the tracking unit 10) to the position sensor(s) 14. Alternatively, the instrument markers 52 may comprise a radio opaque material that is identified and trackable by the position sensor(s) 14. In other configurations, active tracking markers can be employed. The active tracking markers can be, for example, light emitting diodes transmitting light, such as infrared light. Active and passive arrangements are possible. The instrument markers 52 may be arranged in a defined or known position and orientation relative to the other instrument markers 52 in order to allow the surgical navigation system 20 to determine the position and orientation (pose) of the surgical instrument 50. For example, the instrument markers 52 may be registered to the surgical instrument 50 to allow the surgical navigation system 20 to determine the position and/or orientation of a tip 54 or tool portion of the surgical instrument 50 within a defined space, such as the surgical field.

The surgical navigation system 20 may further comprise a patient tracker 40, wherein the patient tracker 40 may be configured to localize a patient 60 in space, such as the surgical field. The patient tracker 40 may comprise an attachment member 44 configured to secure the patient tracker 40 to the patient 60. The attachment member 44 may comprise a clamp, adhesive, strap, threaded fastener, or other similar attachment device. For example, the attachment member 44 may comprise a clamp configured to be secured to the patient 60. This may include utilizing a clamp to secure the patient tracker 40 to a vertebra of the patient 60 proximate to a region of interest 62. This may allow the tracking unit 10 to determine the position and/or orientation of the patient's spine during spinal surgery. Alternative, the attachment 44 may comprise a strap, wherein the strap is configured to encircle and secure the patient tracker to the patient's head. This may allow the tracking system to determine the position and/or orientation of the patient's head during neurosurgery.

The patient tracker 40 may further comprise one or more patient markers 42 configured to be detectable by the position sensors 14 of the tracking unit 10. The patient tracker 40 may be configured to comprise passive tracking elements or patient markers 42 (e.g., reflectors) for transmitting light signals (e.g., reflecting light emitted from the tracking unit 10) to the position sensor(s) 14. Alternatively, the patient markers 42 may comprise a radio opaque material that is identified and trackable by the position sensor(s) 14. The patient markers 42 may be arranged in a defined or known position and orientation relative to the other patient markers 42 in order to allow the surgical navigation system 20 to determine the position and orientation (pose) of the patient 60 and/or region of interest 62. In other configurations, active tracking markers can be employed. The active markers can be, for example, light emitting diodes transmitting light, such as infrared light. Active and passive arrangements are possible. The patient markers 42 may be arranged in a defined or known position and orientation relative to the other patient markers 42 in order to allow the surgical navigation system 20 to determine the position and orientation (pose) of the patient 60 and/or region of interest 62.

Referring to FIGS. 1A and 1B, the head-mounted display (HMD) 30 may be employed in addition to or as an alternative to one or more of the display(s) 22 to enhance visualization before, during, and/or after surgery. The HMD 30 can be used to visualize the same objects described as being visualized on the display(s) 22 and can also be used to visualize other objects, features, instructions, warnings, etc. The HMD 30 can be used to assist with locating and or visualizing target objects related to the medical procedure. The HMD 30 can also be used to visualize instructions and/or warnings, among other uses, as described further below.

The HMD 30 may be a HoloLens® provided by Microsoft Corporation, which is referred to as a mixed or augmented reality HMD owing to its overlay of augmented reality visualizations or computer-generated images onto the real world. It should be appreciated that any reference to augmented reality encompasses mixed reality. Thus, in the configuration described herein, the HMD 30 provides a computational holographic display. Other types of mixed/augmented reality HMDs may also be used, such as those that overlay computer-generated images onto video images of the real world. The HMD 30 may comprise a cathode ray tube display, liquid crystal display, liquid crystal on silicon display, or organic light-emitting diode display. The HMD 30 may comprise see-through techniques like those described herein comprising a diffractive waveguide, holographic waveguide, polarized waveguide, reflective waveguide, or switchable waveguide.

The HMD 30 comprises a head-mountable structure 32, which may be in the form of an eyeglass and may include additional headbands 38 or supports to hold the HMD 30 on the user's head. In other embodiments, the HMD 30 may be integrated into a helmet or other structure worn on the user's head, neck, and/or shoulders.

The HMD 30 has a visor 32 and a lens/waveguide 36 arrangement. The lens/waveguide 36 arrangement is configured to be located in front of the user's eyes when the HMD 30 is placed on the user's head. The waveguide transmits the augmented reality visualizations or images (also referred to as computer-generated images, virtual images, or holographic images) to the user's eyes while at the same time, real images may be seen through the lens/waveguide 36 (it being transparent) such that the user sees a mixed or augmented reality including both real and virtual objects.

Referring to FIG. 1B, the HMD 30 may further comprise a head-mounted display controller (HMD controller) 180 that is configured to be in communication with the navigation controller 80 of the surgical navigation system 20. The HMD controller 180 may comprise an image generator that may be configured to generate the augmented reality visualizations and that transmits those visualizations to the user through the lens/waveguide 36 arrangement. The HMD controller 180 may control the transmission of the augmented reality visualizations to the lens/waveguide 36 arrangement of the HMD 30. The HMD controller 180 may be a separate computer that is located remote from the HMD 30. Alternatively, the HMD controller 180 may be integrated into the head-mountable structure 32 of the HMD 30. The HMD controller 180 may be a laptop computer, desktop computer, microcontroller, or the like with memory, one or more processors (e.g., multi-core processors), input inputs I, output devices (fixed display in addition to HMD 30), storage capability, etc.

The HMD 30 comprises one or more head-mounted display markers or HMD markers 34 that are configured to be detectable by the position sensor(s) 14 of the tracking unit 10. The HMD 30 may be configured to comprise passive tracking elements or HMD markers 34 (e.g., reflectors) for transmitting light signals (e.g., reflecting light emitted from the tracking unit 10) to the position sensor(s) 14. Alternatively, the HMD markers 34 may comprise a radio opaque material that is detectable and trackable by the position sensor(s) 14. In other configurations, active tracking markers can be employed. The active markers can be, for example, light emitting diodes transmitting light, such as infrared light. Active and passive arrangements are possible. The HMD markers 34 may be arranged in a defined or known position and orientation relative to the other HMD markers 34 in order to allow the surgical navigation system 20 to determine the position and orientation (pose) of the HMD 30 within a defined area, such as the surgical field.

The HMD 30 may also comprise a photo and/or video camera 170 in communication with the HMD controller 180. The camera 170 may be used to obtain photographic or video images with the HMD 30, which can be useful in identifying objects or markers attached to objects, as will be described further below.

The HMD 30 may further comprise an inertial measurement unit (IMU) 176 in communication with the HMD controller 180. The IMU 176 may comprise one or more 3-D accelerometers, 3-D gyroscopes, and other sensors to assist with determining a position and/or orientation of the HMD 30 in the HMD coordinate system or to assist with tracking relative to other coordinate systems. The HMD 30 may also comprise an infrared motion sensor 178 to recognize gesture commands from the user. Other types of gesture sensors are also contemplated. The infrared motion sensor 178 may be arranged to project infrared light or other light in front of the HMD 30 so that the infrared motion sensor 178 is able to sense the user's hands, fingers, or other objects for purposes of determining the user's gesture command and controlling the HMD 30, HMD controller 180, and/or navigation controller 80, accordingly.

While FIG. 1A only includes a single individual or surgeon wearing an HMD 30, it is further contemplated that a plurality of HMDs 30 may be configured to be in communication with the surgical navigation system 20. For example, an entire surgical team may wear HMDs 30. In some configurations, such as those in which video cameras 170 are integrated into the HMDs 30 to provide point of view (POV) video, through the POV video stream analysis or simpler context awareness mechanisms (e.g., sensory-based feedback, heuristics based on inputs from isolated sensors, etc.), a computer-based model of the surgical context can provide participant-specific mixed/augmented reality aids to facilitate the current task being performed by the individual participant or help prepare for their next contribution to the surgical or medical procedure.

In one configuration, two or more participants and their HMDs 30 can be linked together in conjunction with the contextual information of the medical procedure. The participants may be linked by sharing their current POV or in a more inherent way, by sharing the objects of interest being addressed at any given point in time by any of the participants. Within this configuration, a first participant is able to enhance his or her personal assessment of a second participant's circumstances through the display of mixed/augmented reality aids as the first participant directs his/her personal POV to that of the second participant. As the first participant realizes an opportunity for optimization or altering the planned medical procedure, the appropriate interplay with the different participants or surgical environment can take place. This interaction can be directly executed by the first participant or can be facilitated through mixed/augmented reality aids or other computer-assisted aids, which in turn can be automatically generated or created by the first participant to support the second participant's course of action.

Figure 2:
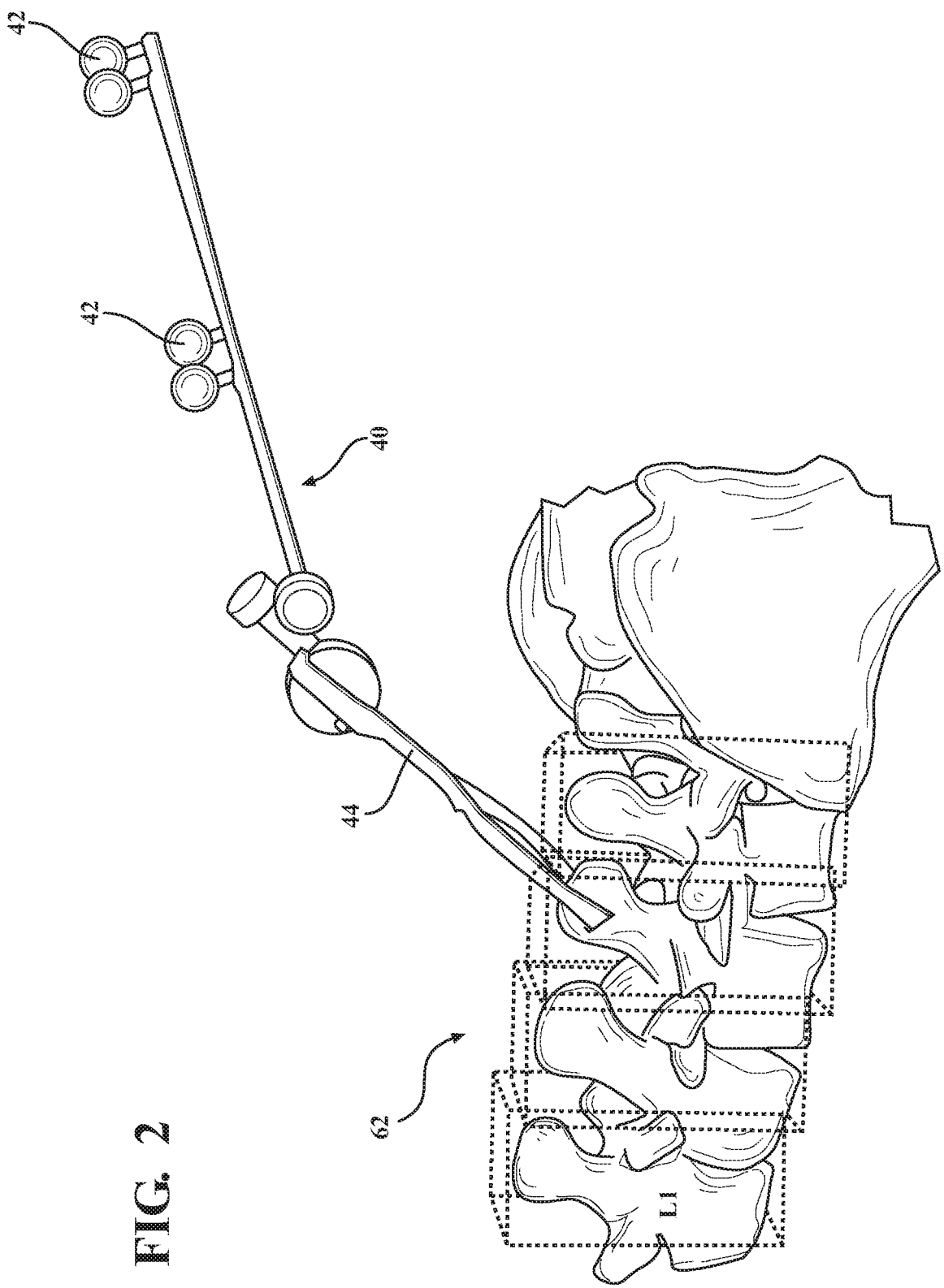
FIG. 2 is a perspective view of a patient tracker of the surgical tracking unit of FIG. 1A, the patient tracker coupled to a patient proximate to a region of interest.

Referring to FIG. 2, an example representation of an augmented reality visualization of the region of interest 62 as perceived by the user through the lens 36 of the HMD 30 is illustrated. As illustrated in FIG. 2, the patient tracker 40 may be coupled or secured to the patient 60 via the attachment member 44. This will allow the tracking unit 10 to identify the position and/or orientation of the patient 60 and/or region of interest 62 relative to the HMD 30 for the purpose of generating and orienting the appropriate augmented reality visualization on the lens 36 so that the virtual portion of the image may be properly overlaid on the real portion of the patient 60 as viewed through the lens 36. While only a single patient tracker 40 is illustrated in FIGS. 1A and 2, it is further contemplated that additional patient trackers 40 may be coupled to or attached to the patient 60. The use of additional patient trackers 40 may allow the position and/or movement of multiple portions of the patient 60 and/or regions of interest 62 to be tracked. The use of multiple patient trackers 40 may also increase the accuracy of tracking the position and/or movement of the patient 60 and/or region of interest 62.

The augmented reality visualization of the region of interest 62 may comprise both an augmented reality boundary visualization and/or combined boundary with augmented reality textual label. For example, as illustrated in FIG. 2, augmented reality boundary visualizations are shown as cubes enclosing individual vertebrae as projected or displayed on the lens 36 of the HMD 30, as viewed by the user when observing the patient's 60 actual spine through the lens 36. The augmented reality boundary visualizations may further be identified to the user on the lens 36 of the HMD 30 by the augmented reality textual labels, such as L1. For example, as illustrated in FIG. 2, "L1" is included in the augmented reality visualization projected on the lens 36 of the HMD 30 to identify the specific vertebrae enclosed by the augmented reality boundary visualization. While only a single augmented reality textual label is illustrated in FIG. 2, it should be understood that a plurality of additional augmented reality textual labels may be included as part of the augmented reality visualization to label and/or identify additional features or objects to the user of the HMD 30.

Figure 3:
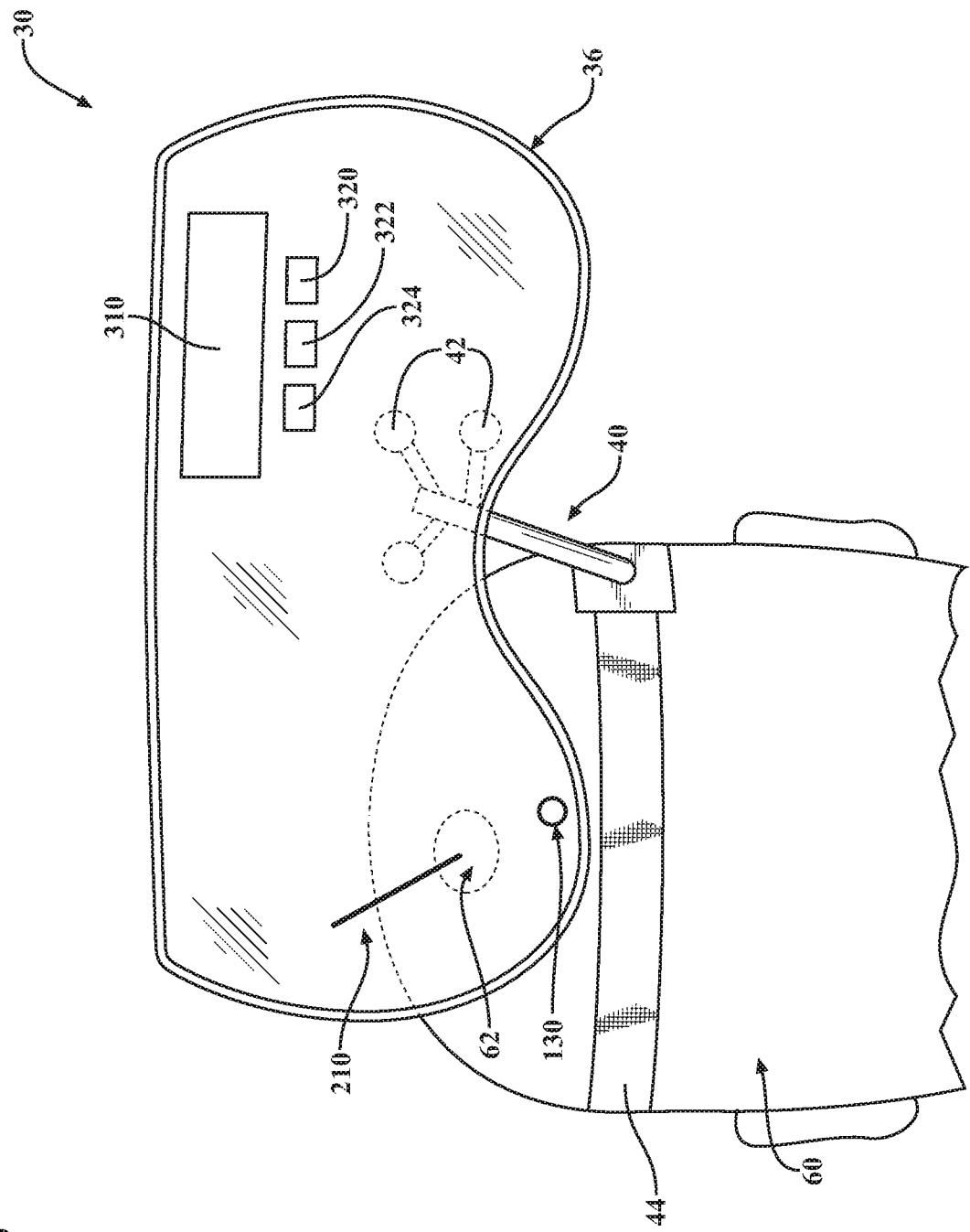
FIG. 3 is a schematic view of a first configuration of an augmented reality visualization projected on the lens of the head-mounted display of FIG. 1A, the augmented reality visualization projected on the lens including virtual images overlaid on live features that are illustrated in phantom.

Referring to FIG. 3, an additional configuration of the augmented reality visualization as perceived by the user through the lens 36 of the HMD 30 is illustrated. In the example configuration illustrated in FIG. 3, the user is viewing a portion of the patient's 60 head through the lens 36 of the HMD 30. For example, FIG. 3 may represent the augmented reality visualization as seen by a surgeon performing a neurosurgery procedure, such as removing a tumor. Within the lens 36, the items illustrated in phantom, i.e., using dotted lines, represent the real features that may be seen by the user. This may include a portion of the patient's 60 head, as well as an incision site or region of interest 62. The user may also be able to see a portion of the patient tracker 40, attachment member 44, and/or the patient markers 42 through the lens 36 of the HMD 30.

The user of the HMD 30 may also observe a number of augmented reality visualizations, which are illustrated within the lens 36 of FIG. 3 using solid lines. One such augmented reality visualization may include a target object representing a single point-shaped landmark related to the medical procedure. For example, as illustrated in FIG. 3, the target object 130 may represent an item within the patient 60 that is to be operated on during the medical procedure, such as a tumor or organ. Alternatively, the target object 230 may represent a medical device or implant to be inserted in the patient 60 during the medical procedure, which will be discussed in detail below.

The augmented reality visualization may also comprise a target trajectory axis 210. The target trajectory axis 210 may represent a planned or intended surgical path. For example, the target trajectory axis 210 may represent the optimal or preferred angle or direction for aligning and/or inserting the surgical instrument 50 during execution of the medical procedure. The target trajectory axis 210 may be defined by a solid or intermittent line connecting a target object 130, 230 and an entry point or insertion point proximate to the region of interest 62.

The augmented reality visualization may further comprise an augmented reality window, indicator, or text box 310. The augmented reality window 310 may comprise a window displayed on the lens 36 of the HMD 30. The augmented reality window 310 may be configured to display the patient data, such as a pre-operative image or scan. The augmented reality window 310 may also be configured to display an image of the planned surgical procedure, including identifying any critical items such as nerves, organs, or similar elements the user may want to be aware of when performing the medical procedure. For example, when inserting a screw in the patient's 60 vertebrae, the image may include nerve endings to avoid. The augmented reality window 310 may also include text or indicia related to the medical procedure. For example, the augmented reality window 310 may include notes related to the medical procedure, such as facts specific to the patient's 60 medical condition. Alternatively, the augmented reality window 310 may also include text of information related to the distance the surgical instrument 50 is from the patient 60, the region of interest 62, the target object 130, 230, and/or the target trajectory axis 210.

The augmented reality visualization may also comprise one or more control buttons 320, 322, 324 to be displayed on the lens 36 of the HMD 30. The one or more control buttons 320, 322, 324 may be configured to allow the user to manipulate the augmented reality visualization displayed on the lens 36. For example, the user may use hand and/or facial gestures or movements, as described above, to select or activate one of the control buttons 320, 322, 324. The control buttons 320, 322, 324 may be configured to adjust the contrast, transparency, and/or color of the augmented reality visualization on the lens 36. The control buttons 320, 322, 324 may also be used to manipulate or enhance the information displayed on the lens 36. For example, the control buttons 320, 322, 324 may be configured to zoom in and/or zoom out on the patient data displayed in the augmented reality window 310. This may include zooming in on a pre-operative image or scan of the patient 60 to allow the user to better visualize the area proximate to the target object 130, 230. The control buttons 320, 322, 324 may further be configured to rotate or move an image of the patient data. This may include moving the position and/or location the augmented reality window 310 is displayed on the lens 36 to avoid blocking or interfering with the user's view of the augmented reality visualization on the patient 60.

Figure 4:
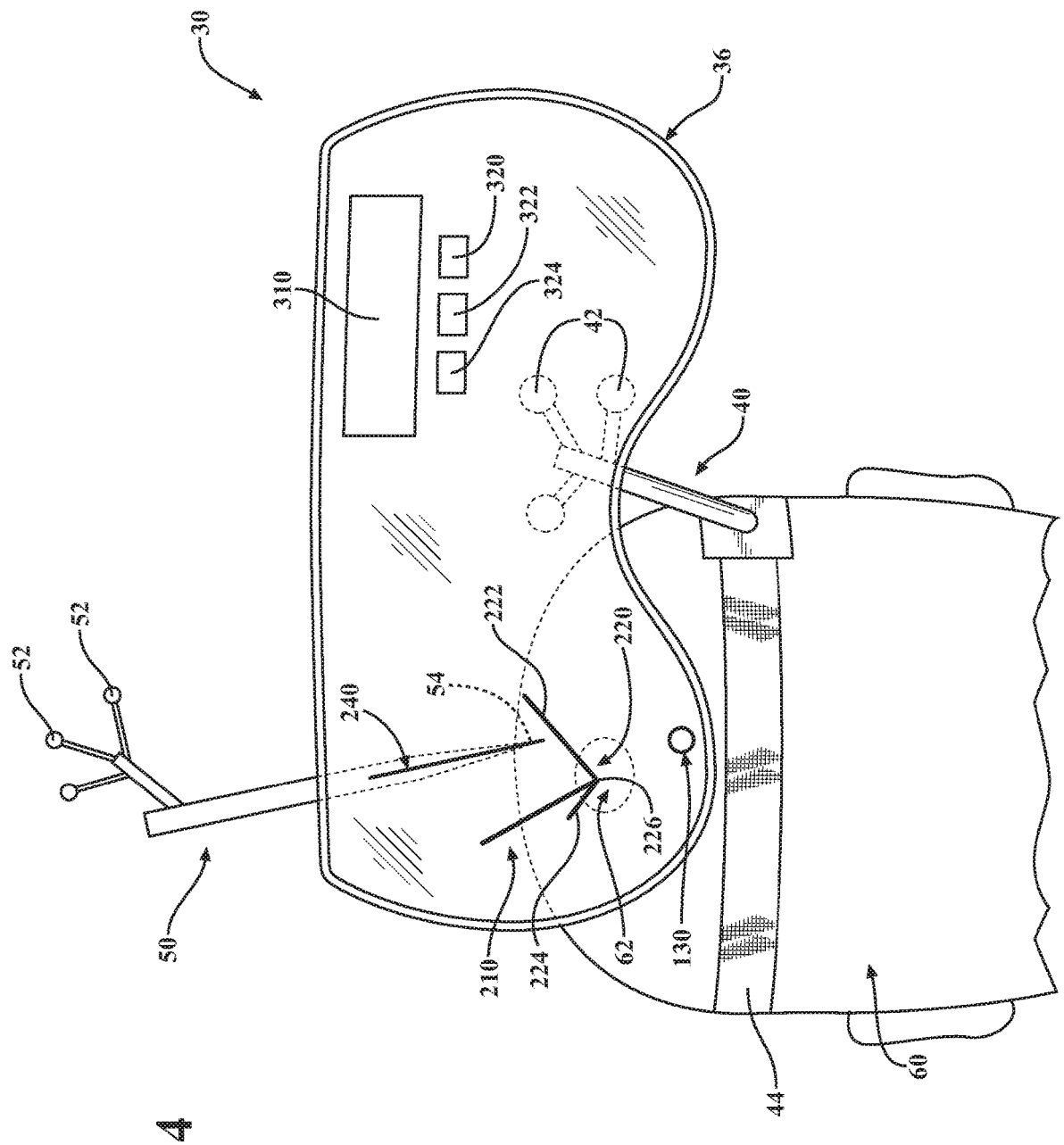
FIG. 4 is a schematic view of a second configuration of an augmented reality visualization projected on the lens of the head-mounted display of FIG. 1A, the augmented reality visualization projected on the lens including virtual images overlaid on live features that are illustrated in phantom.

FIG. 4 comprises another configuration of the augmented reality visualization as perceived by the user through the lens 36 of the HMD 30 including the surgical instrument 50. Similar to examples described above, the augmented reality visualization may comprise the target trajectory axis 210, the target object 130, the augmented reality window 310 and/or the control buttons 320, 322, 324. However, the augmented reality visualization may further comprise an instrument axis 240. The instrument axis 240 may be defined by a line starting at the tip 54 of the surgical instrument 50 and extending from the tip 54 along the normal axis of surgical instrument 50, wherein the normal axis generally bisects the surgical instrument 50. For example, as illustrated in FIG. 4, the instrument axis 240 is defined by a line that starts at the tip 54 of the surgical instrument 50 and extends generally parallel to a longitudinal axis that bisects the surgical instrument 50. The instrument axis 54 may also project beyond the end or tip 54 of the surgical instrument 50.

The augmented reality visualization illustrated in FIG. 4 further comprises an augmented reality position alignment visualization 220. The augmented reality position alignment visualization 220 comprises two axis-aligned deviation vectors 222, 224 comprising the decomposition of a distance vector from a point on the target trajectory axis 210 to the tip 54 of the surgical instrument 50, or other portion on the surgical instrument 50. Axis-aligned may refer to the line(s) representing the deviation vector(s) 222, 224 being oriented to be parallel to one of the three major axes of a reference coordinate system. Typically, the first deviation vector 222 may be oriented in parallel to a first axis of the reference coordinate system, and the second deviation vector 224 may be oriented in parallel to a second axis of the reference coordinate system. For example, two axis-aligned deviation vectors 222, 224 may refer to the line representing the first deviation vector 222 being oriented to be parallel to the x-axis and the line representing the second deviation vector 224 being oriented to be parallel to the y-axis of the reference coordinate system. The reference coordinate system may be defined relative to the HMD 30, the patient tracker 40, the surgical instrument 50, the tracking unit 10, line of sight of the user, or some other point within the surgical field.

The lines representing the first deviation vector 222 and the second deviation vector 224 may be configured to intersect at an origin point, wherein the first deviation vector 222 and the second deviation vector 224 are positioned to be generally perpendicular to one another. The origin of the first deviation vector 222 and the second deviation vector 224 may be positioned and/or located on or along the target trajectory axis 210. Alternatively, the origin of the first deviation vector 222 and the second deviation vector 224 may be positioned and/or located proximate the tip 54 of the surgical instrument 50. In yet another configuration, the origin of the first deviation vector 222 and the second deviation vector 224 may be positioned and/or located within the augmented reality window 310 or floating on the lens 36 of the head-mounted display 30.

The first deviation vector 222 may be defined by the lateral and/or horizontal position of the tip 54 of the surgical instrument 50 relative to the target trajectory axis 210 and/or target object 130. The second deviation vector 224 may be defined by the longitudinal and/or vertical position of the tip 54 of the surgical instrument 50 relative to the target trajectory axis 210 and/or target object 130. The size and/or length of the first deviation vector 222 and/or the second deviation vector 224 may be indicative of the distance or deviation of the surgical instrument 50 relative to the target trajectory axis 210 in the direction of the respective deviation vector 222 or 224. For example, the longer the line representing the first deviation vector 222 or the second deviation vector 224, the further the surgical instrument 50 may be positioned from the target trajectory axis 210. Alternatively, the shorter the line representing the first deviation vector 222 or the second deviation vector 224, the closer the surgical instrument 50 is positioned from the target trajectory axis 210. It is also contemplated that the lack of a line representing the first deviation vector 222 or the second deviation vector 224 is indicative that the surgical instrument 50 is properly positioned and/or aligned in the direction corresponding with the absent deviation vector 222, 224. The two axis-aligned deviation vectors 222, 224 may assist the user in correctly positioning and/or aligning the surgical instrument 50 relative to the target trajectory axis 210 and/or the target object 130. For example, the two axis-aligned deviation vectors 222, 224 comprising the augmented reality position alignment visualization 220 are configured to inform the user of the relative location of the surgical instrument 50 relative to the target trajectory axis 210.

In each of the various configurations of the augmented reality visualizations, the augmented reality visualizations may be scaled to allow the user to see additional details. The scaling may also allow the user to see smaller deviations. Referring to FIG. 4, the two axis-aligned deviation vectors 222, 224 of the augmented reality position alignment visualization 220 may be sized and/or scaled to allow the user to see smaller deviations. For example, the length of the first deviation vector 222 and/or the second deviation vector 224 may be scaled by a factor of K, wherein a small deviation of two millimeters between the target trajectory axis 210 and the tip 54 of the surgical instrument 50 may be represented by a one inch long line representing the first deviation vector 222 and/or second vector 224 displayed on the lens 36.

In another example, the decomposition of the distance vector into the two axis-aligned deviation vectors 222, 224 illustrated in FIG. 4 may be made based on two eigenvectors derived from: the two of the three primary patient axes with the highest angle to the target trajectory axis 210, or the line of sight axis being projected onto the plane perpendicular to the target trajectory axis 210 and attached to the closest point on the target trajectory axis 210 from the tip 54 of the surgical instrument 54, and the perpendicular vector in the same plane to the projected line of sight axis. The decomposition of the distance vector into two axis-aligned deviation vectors comprising the augmented reality position alignment visualization 220 may be computed based on to two eigenvectors. For example, the two eigenvectors may be based on two of the three primary patient axes of a patient coordinate system with the highest angle to the target trajectory axis 210. The primary patient axes of the patient coordinate system may be derived from the patient data, such as a 3D image data set which was previously registered to the patient tracker 40. Alternatively, the two eigenvectors may be based on a reference coordinate system defined by the line of sight of the user with the intention to increase the distinguishability of the first deviation vector 222 and/or the second deviation vector 224 as part of the augmented reality position alignment visualization 220 for the surgeon. This may be helpful if the viewing direction of the user is nearly perpendicular to the target trajectory axis 210. The reference coordinate system may be derived from the plane perpendicular to the target trajectory axis 210 and attached to the closest point on the target trajectory axis 210 from the tip 54 of the surgical instrument 50, and the line of sight of the surgeon. It is also conceivable that the two eigenvectors may be based on a combination of both the primary patient axes of a patient coordinate system and the reference coordinate system defined by the line of sight of the user.

In one configuration, the distance between the surgical instrument 50 and the target trajectory axis 210 is computed based on the distance of the tip 54 of the surgical instrument 50 to at least one location selected from the group of: a segment connecting the target object 130, 230 and an entry point of the target trajectory axis 210, a line connecting the target object 130, 230 and the entry point of the target trajectory axis 210, and the target object 130, 230 or the entry point of the target trajectory axis 210.

Figure 5:
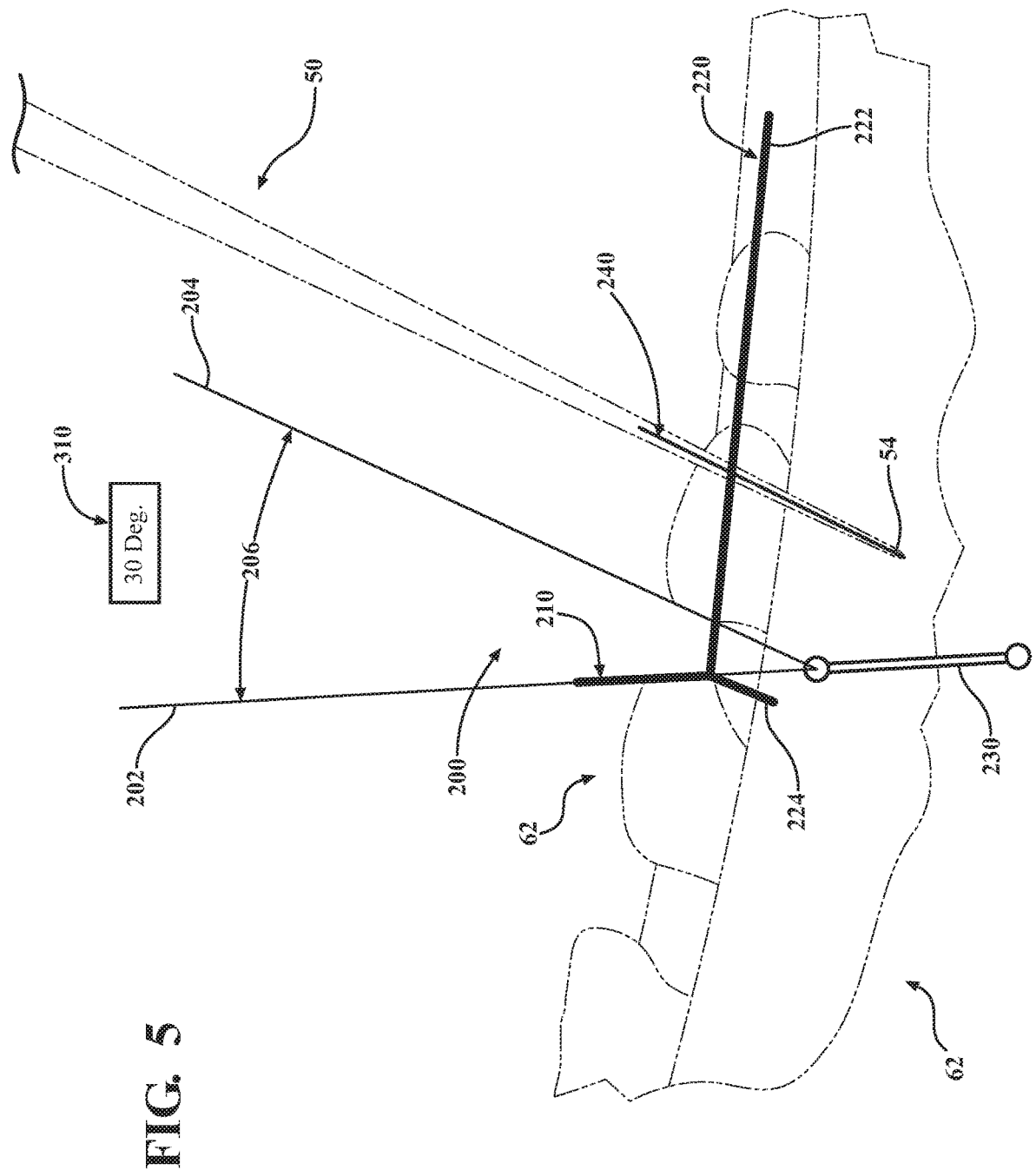
FIG. 5 is an enhanced view of an exemplary augmented reality visualization as depicted on the head-mounted display during a surgical procedure including the surgical tool.

Referring to FIG. 5, another configuration of the augmented reality visualization from the perspective of the user looking through the lens 36 of the HMD 30 is illustrated. As described above, with regard to FIG. 4, the augmented reality visualization may comprise the augmented reality position alignment visualization 220. The augmented reality visualization may also comprise an augmented reality angular alignment visualization 200. The augmented reality angular alignment visualization 200 may comprise a deviation angle 206 which represents the angle between a first angular vector 204 representative of an axis offset and in parallel with the instrument axis 240 and a second angular vector 202 representative of the target trajectory axis 210. For example, the augmented reality angular alignment visualization 200 is illustrated as a first angular vector 204 representing an axis that is offset and in parallel with the instrument axis 54 of the surgical instrument 50 and a second angular vector 202 representing the target trajectory axis 210. The first angular vector 204 and the second angular vector 202 may be connected by an arc representative of the deviation angle 206 between the first angular vector 204 and the second angular vector 202. This may represent the deviation angle 206 between the target trajectory axis 210 and the instrument axis 54. As described above, the target trajectory axis 210 may be defined by a line connecting a target object 130, 230 and an entry point or insertion point proximate to the region of interest 62. For example, as illustrated in FIG. 5, the target object 230 may comprise image of a screw overlaid on the patient in the planned position. This may include an overlaid image of the screw 230 where it is to be inserted into a vertebra of the patient 60. The augmented reality visualization may further comprise the augmented reality window 310, as described above, wherein the augmented reality window 310 comprises a label, text, or similar indicia identifying the deviation angle 206 between the first angular vector 204 and the second angular vector 202. For example, the augmented reality window 310 may be positioned proximate to the augmented reality angular alignment visualization 200 and configured to display a text label identifying the deviation angle 206. The text label displayed in the augmented reality window 310 may include "30 Degrees", "1 Radian", or similar angular measurement.

In another example, the visualization of the deviation angle 206 comprises: a position corrected augmented reality visualization of the instrument axis 240, the target trajectory axis 210 and an arc connecting proximal ends of both the instrument axis 240 and the target trajectory axis 210, or an axonometry of the position corrected augmented reality visualization. Axonometry is a graphical procedure belonging to descriptive geometry that generates a planar image of a three-dimensional object. The term "axonometry" can be defined as "to measure along axes", and may indicate that the dimensions and scaling of the coordinate axes are important. The result of an axonometric procedure is a uniformly-scaled parallel projection of the object.

In the example configuration illustrated in FIG. 5, the target object 230 comprises an augmented reality visualization of the planned location for a screw to be inserted in a vertebra of the patient 60, and the second angular vector 202 is representative of the orientation of the target trajectory axis 210 for inserting the screw in the identified location. The augmented reality visualization of the target object 230 raises spatial awareness when in situations where the real surgical target is hidden from the surgeon's view. Furthermore, the arc representing the deviation 206 connecting the first angular vector 204 representing the instrument axis 240 of the surgical instrument 50 relative to the target object 230 and the second angular vector 202 representing the target trajectory axis 210 provides a visual cue to the user of an approximation for correcting the deviation of the angle 206 between the first angular vector 204 and second angular vector 202.

The augmented reality angular alignment visualization 200 may also be scaled to allow the user to more easily see smaller deviations in the deviation angle 206. For example, as illustrated in FIG. 5, the length of the line representing the first angular vector 204 and/or the length of the line representing the second angular vector 202 may be scaled by a factor of K to exaggerate the line representing the first angular vector 204 and the second angular vector 202 to allow the user to more easily see smaller deviations in the deviation angle 206 represented by the arc. The scaling of the length of the line representing the first angular vector 204 and/or the length of the line representing the second angular vector 202 is typically chosen that the visualized length of the first angular vector 204 and/or the length of the line representing the second angular vector 202 corresponds to several centimeters. In case of additional visualization of the target object 130, 230, such as a pedicle screw, the length of the line representing the first angular vectors 204 and/or the second angular vector 202 may also depend on the length/size of this target object 130, 230. Scaling may also include scaling the line representing the first angular vector 204 and/or the line representing the second angular vector 202 to increase the length of the line representing the first angular vector 204 and/or the line representing the second angular vector 202. Alternatively, this may also include scaling the line representing the first angular vector 204 and/or the line representing the second angular vector 202 to decrease the length of the line representing the first angular vector 204 and/or the line representing the second angular vector 202 to reduce the size of the augmented reality angular alignment visualization 200 on the lens 36. This may prevent the augmented reality angular alignment visualization 200 from obstructing or interfering with the user's view.

In another example, the decomposition of the deviation angle 206 may be scaled relative to the two eigenvectors derived from: the two of the three primary patient axes with the highest angle to the target trajectory axis 210, or the line of sight axis being projected onto the plane perpendicular to the target trajectory axis 210 and attached to the closest point on the target trajectory axis 210 from the tip 54 of the surgical instrument 50, and the perpendicular vector in the same plane to the projected line of sight axis. As described above, the two eigenvectors may be based on two of the three primary patient axes of a patient coordinate system with the highest angle to the target trajectory axis 210. Alternatively, the two eigenvectors may be based on a reference coordinate system defined by the line of sight of the user with the intention to increase the distinguishability of the first deviation vector 222 and/or the second deviation vector 224 as part of the augmented reality position alignment visualization 220 for the surgeon. This may be helpful if the viewing direction of the user is nearly perpendicular to the target trajectory axis 210.

Furthermore, it should be understood that the various configurations of the augmented reality visualizations described above may include highlighting and/or color schemes to allow the user to distinguish between the various types of augmented reality visualizations. For example, augmented reality position alignment visualization 220 may be displayed on the lens 36 of the HMD 30 in a first color, and the augmented reality angular alignment visualization 200 may be displayed on the lens 36 of the HMD 30 in a second color. The first color and the second color may be selected to be distinguishable from one another. The distinguishable and/or different colors for the various features or elements of the augmented reality visualizations may be selected from a base color of a trajectory by equidistant placing of alternate colors in a chromaticity space around a white point and selecting their dominant wavelength by extrapolation. The colors may be selected from high-luminance complementary colors selected from the group comprising yellow, pink, green and cyan. Referring back to FIG. 5, in a non-limiting example, the first deviation vector 222 and the second deviation vector 224 of augmented reality position alignment visualization 220 may be displayed on the lens 36 of the HMD 30 as purple colored lines. By contrast, the first angular vector 204 and the second angular vector 202 of augmented reality angular alignment visualization 200 may be displayed on the lens 36 of the HMD 30 as blue or cyan colored lines. A different color may similarly be used to distinguish the target trajectory axis 210 from the other visualization. For example, the target trajectory axis 210 may be displayed on the lens 36 of the HMD 30 as a yellow colored line. It should be understood that it is contemplated that any combination of colors may be utilized for each of the various augmented reality visualizations to distinguish them from one another.

The augmented reality visualization described above may also be distinguishable as displayed on the lens 36 of the HMD 30 by varying the transparency and/or opacity of each augmented reality visualization. For example, augmented reality visualization may be configured such that the augmented reality position alignment visualization 220 may be displayed on the lens 36 of the HMD 30 with opaque lines, and the augmented reality angular alignment visualization 200 may be displayed on the lens 36 of the HMD 30 as an at least partially transparent line or completely hidden from view. In another example, wherein the augmented reality visualization comprises a plurality of trajectories and/or axes, all trajectories and/or axes except the one with the minimum distance from the instrument axis 240 and/or the tip 54 of the surgical instrument 50 may be displayed with increased transparency. This eliminates unnecessary or less important augmented reality visualizations from the view of the user.

The line type may similarly be utilized to distinguish the various augmented reality visualizations described above. Referring back to FIG. 5, in a non-limiting example, the first deviation vector 222 and the second deviation vector 224 of augmented reality position alignment visualization 220 may be displayed on the lens 36 of the HMD 30 as a solid line having a defined line weight. By contrast, the first angular vector 204 and the second angular vector 202 of augmented reality angular alignment visualization 200 may be displayed on the lens 36 of the HMD 30 as a solid line having a line weight that is different from the line weight of the augmented reality position alignment visualization 220. A different line type may similarly be used to distinguish the target trajectory axis 210 from the other visualization. For example, the target trajectory axis 210 may be displayed on the lens 36 of the HMD 30 as a dashed, dotted, or similarly distinct line type. It should be understood that is it contemplated that any combination of line types may be utilized for each of the various augmented reality visualizations to distinguish them from one another.

Figure 6:
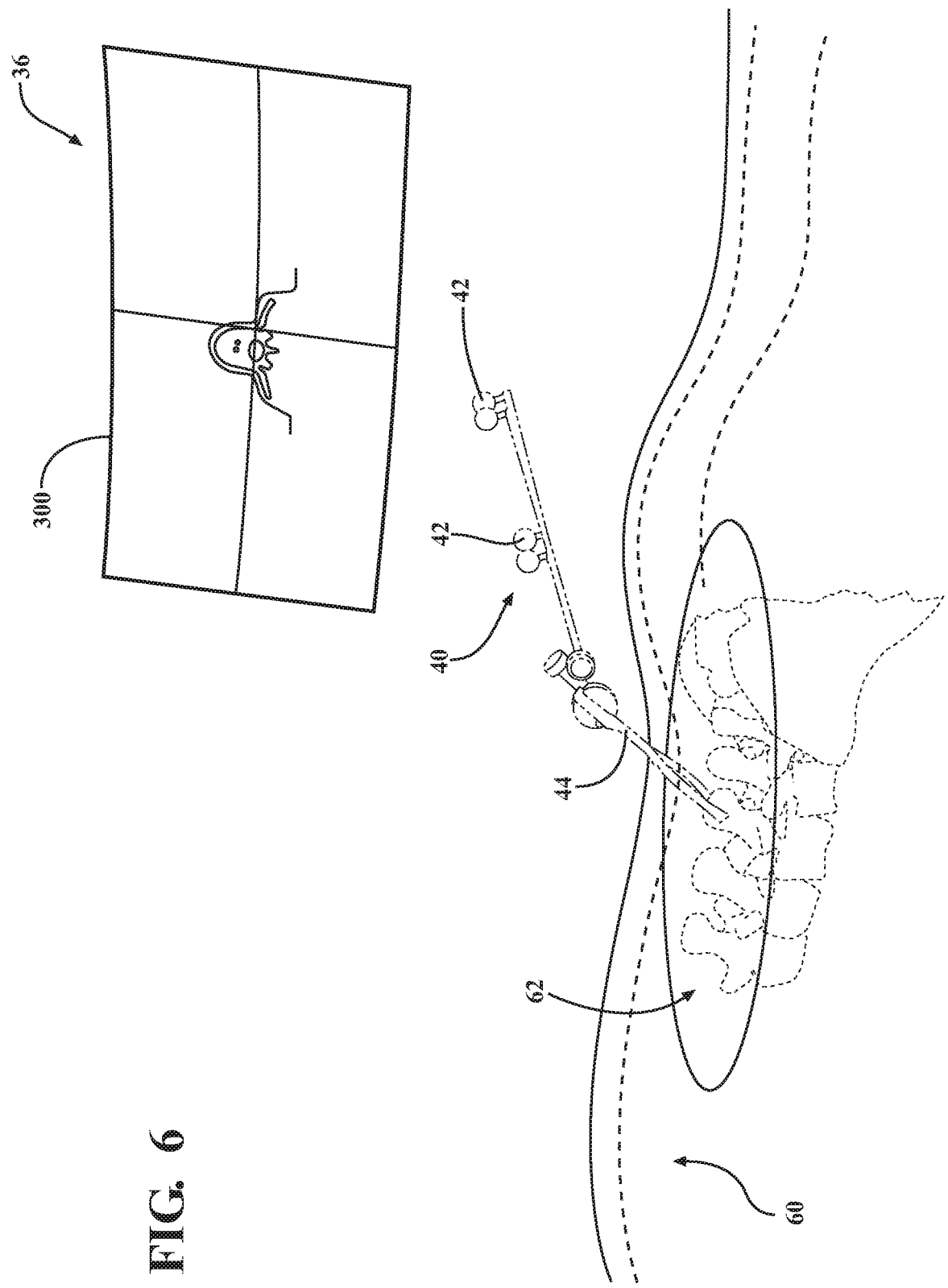
FIG. 6 is an enhanced view of a second exemplary augmented reality visualization as observed by the user on the head-mounted display during a surgical procedure including the patient tracker and a slice of a pre-operative image.

FIG. 6 illustrates an example configuration of the augmented reality visualization comprising only a virtual image as perceived by the user through the lens 36 of the HMD 30. As illustrated in FIG. 6, the augmented reality visualization may comprise a virtual image of a slice of the patient image data shown in a fixed position floating frame 300 above the real surgical site or region of interest 62 as viewed through the lens 36. Similar to examples described above, the user may still view the real features of the patient 60, such as the patient's 60 spine, through the lens 36 of the HMD 30. However, additional information or images, such as patient data, may be displayed in a floating frame 300 on the lens 36. For example, as illustrated in FIG. 6, the augmented reality visualization may comprise an image of a slice of the patient data, such as a two-dimensional image of a specific vertebra. An axis or coordinate system may be overlaid on the slice of the patient data depicted in the floating frame 300. The axis or coordinate system may be configured to represent the position and/or orientation of the surgical instrument 50 relative to the patient data depicted in the floating frame 300.

Figure 7:
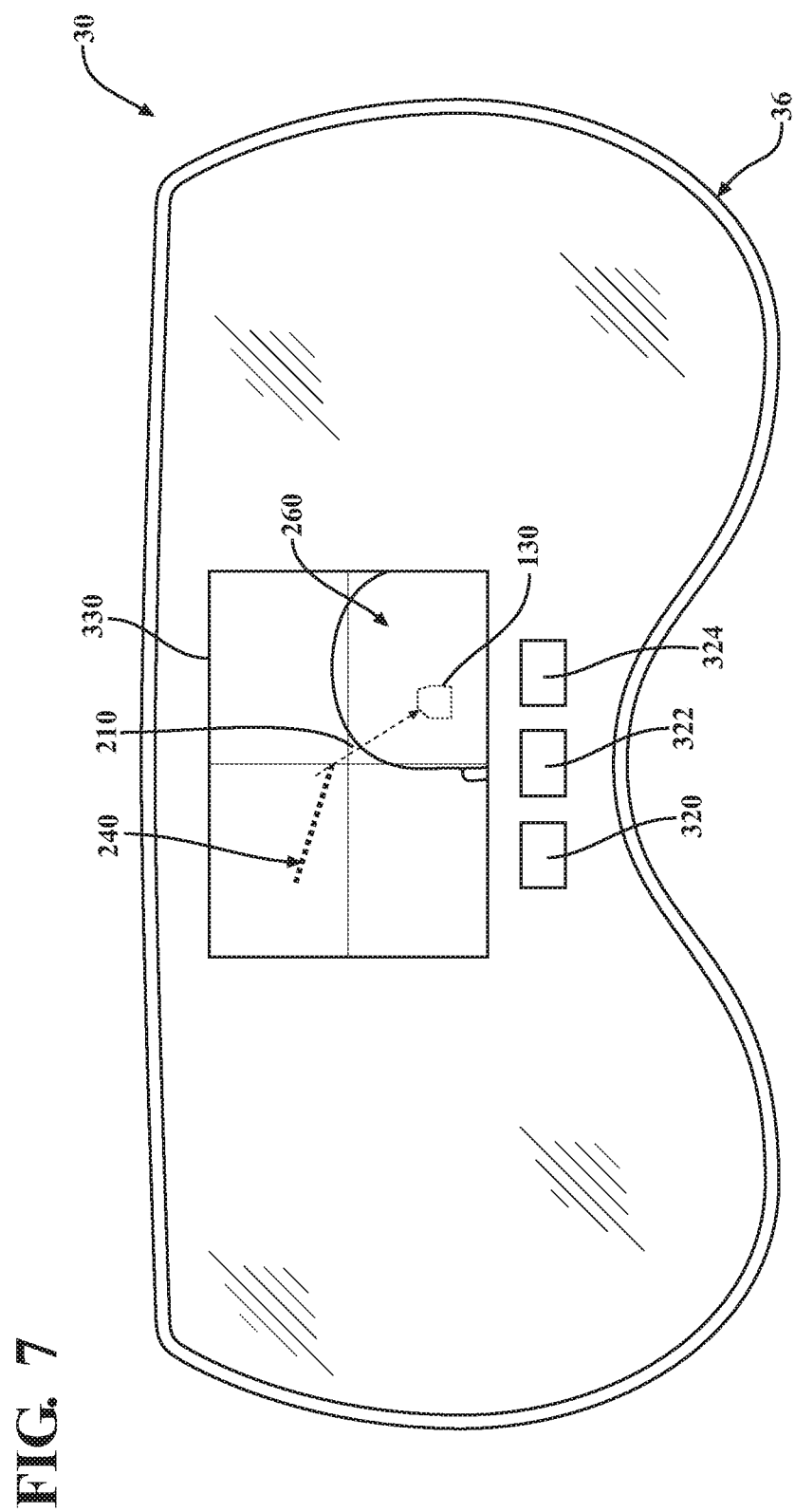
FIG. 7 is a schematic view of a third configuration of an augmented reality visualization projected on the lens of the head-mounted display of FIG. 1A, the augmented reality visualization projected on the lens including a virtual image of pre-operative data illustrated in a display window.

Referring to FIG. 7, in another example configuration of the augmented reality visualization, the augmented reality visualization may comprise a virtual image that is displayed on the lens 36 of the HMD 30 in a display window 330. Different from some of the prior example configurations of augmented reality visualizations described above, the augmented reality visualization illustrated in FIG. 7 is an example of an augmented reality visualization comprising only a virtual image displayed on the lens 36. For example, the augmented reality visualization does not require the user of the HMD 30 to be in view of the patient 60 and/or the region of interest 62. This augmented reality visualization may be displayed on the lens 36 to allow the user to view an image or depiction of the surgical plan overlaid on a virtual image or model of the patient 260. Similar to the floating frame 300 described above, the display window 330 may be configured to depict patient data, such as an image or patient scan. The display window 330 may be further configured to depict the target trajectory axis 210, the instrument axis 240, and/or the target object 130 overlaid on the patient data. As in similar examples described above, the display window 330 of this augmented reality visualization may be manipulated by the user using control button(s) 320, 322, 324. For example, the user may use a hand gesture to select one or more of the control button(s) 320, 322, 324 to zoom-in or zoom-out to get a better visual of the target trajectory axis 210, the instrument axis 240, and/or the target object 130.

Figure 8:
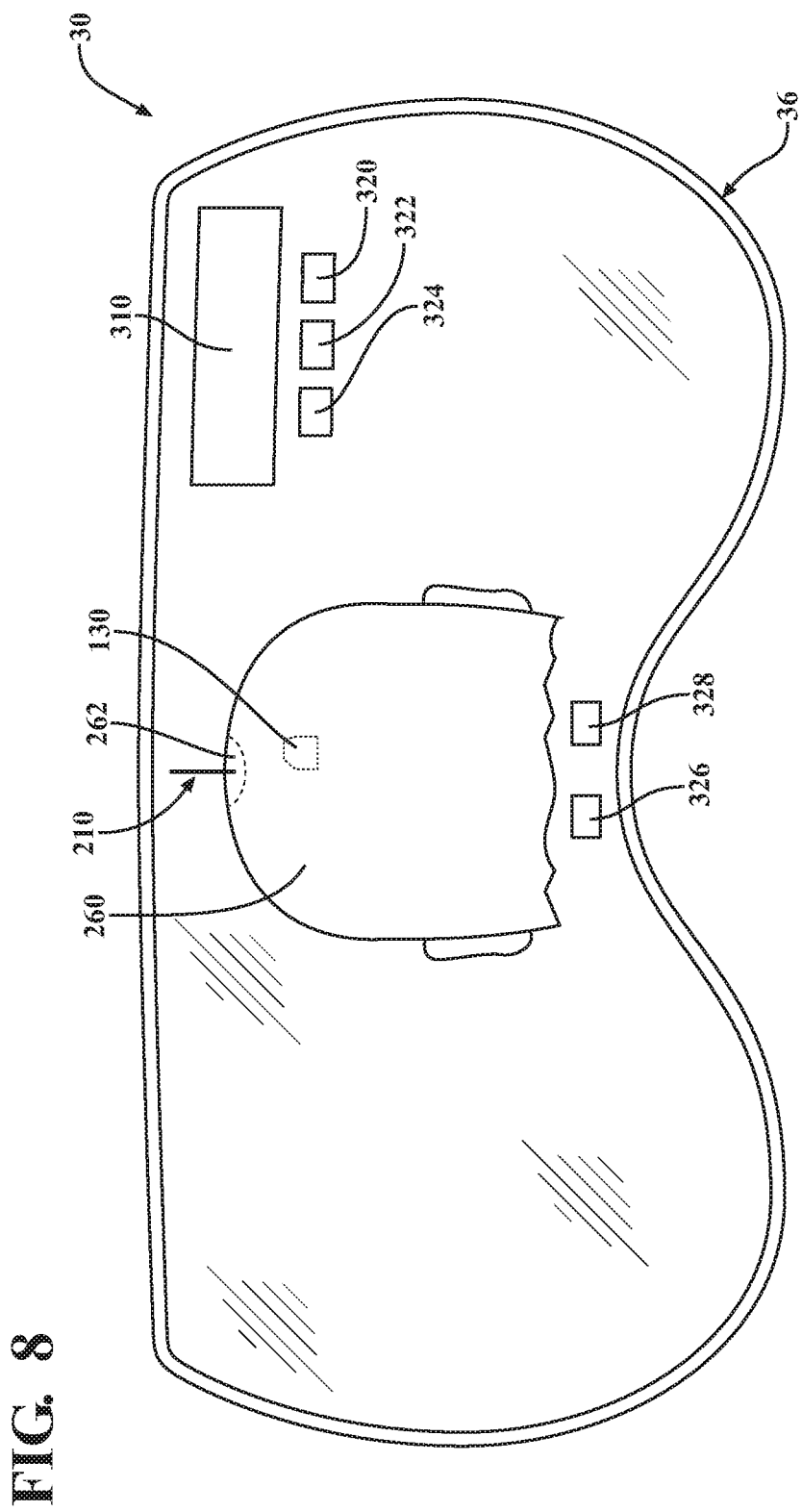
FIG. 8 is a schematic view of a fourth configuration of an augmented reality visualization projected on the lens of the head-mounted display of FIG. 1A, the augmented reality visualization projected on the lens including a virtual image of pre-operative data.

FIG. 8 illustrates another alternative configuration of the augmented reality visualization including a virtual image of a portion of the patient 260 and/or patient data as displayed on the lens 36 of the HMD 30. The portion of the patient 260 and/or patient data displayed on the lens 36 as the augmented reality visualization may include the target trajectory axis 210, region of interest 262, and/or the target object 130. The augmented reality visualization may also comprise a depiction of additional anatomical features and/or a planned surgical pathway overlaid on the patient 260 and/or patient data. For example, the augmented reality visualization may comprise a virtual 3-D image of the patient 260 displayed on the lens 36. This may allow the user to visualize the additional anatomical features and/or the planned surgical pathway on the lens 36 of the HMD 30, as opposed to having to divert their attention to another external display. The augmented reality visualization may further comprise additional control buttons 326, 328, wherein the control buttons 326, 328 are configured to manipulate the augmented reality visualization displayed on the lens 36. For example, one of the control buttons 326, 328 may be configured to zoom-in and/or zoom-out. Additionally, one of the control buttons 326, 328 may be configured to rotate the augmented reality visualization to allow the user to observe or view the augmented reality visualization from a different angle or perspective. When the augmented reality visualization is a virtual 3-D image of the patient 260, the control buttons 326, 328 may be configured to rotate the virtual 3-D model of the patient 260 to allow the user to view the surgical plan and/or target trajectory axis 210 from multiple angles.

A method of aligning the surgical instrument 50 using the surgical navigation system 20 including the head-mounted display 30 described above may comprise planning the target trajectory axis 210 based on patient data registered to the patient tracker 40. The method may further comprise the step of displaying on the head-mounted display 30 the augmented reality position alignment visualization 220 as two axis-aligned deviation vectors 222, 224 comprising the decomposition of a distance vector from a point on the target trajectory axis 210 to a tip 54 of the surgical instrument 50. For example, the method may comprise displaying the first deviation vector 222 and the second deviation vector 224 on the lens 36 of the head-mounted display 30. The first deviation vector 222 and/or the second deviation vector 224 may be displayed as a solid and/or a dotted line. The first deviation vector 222 and the second deviation vector 224 may also be displayed as an arrow.

The method may further comprise the step of displaying on the head-mounted display 30 the augmented reality angular alignment visualization 200 comprising the deviation angle 206 which shows the angle between the first angular vector 204 representative of the instrument axis 240 of the surgical instrument 50 and the second angular vector 202 of the target trajectory axis 210. For example, the method may comprise displaying the first angular vector 204 and the second angular vector 202 as lines connected by an arc representative of the deviation angle 206 between the first angular vector 204 and the second angular vector 202.

The method may also comprise the step of updating the augmented reality position alignment visualization 220 and/or the augmented reality angular alignment visualization 200 displayed on the head-mounted display 30 based on the measurement data of the tracking unit 10 to indicate the relative location of the surgical instrument 50 to the target trajectory axis 210 from the perspectives of the head-mounted display 30. The target trajectory axis 210 may be defined by a line connecting the target object 130, 230 and an entry point. This updating may be continuous.

The method of aligning the surgical instrument 50 may further comprise displaying the augmented reality visualization of the instrument axis 240 of the surgical instrument 50. The instrument axis 240 may be displayed as line or an outline of the surgical instrument 50. The augmented reality visualization of the instrument axis 240 displayed on the lens 36 of the head-mounted display 30 may indicate the position of the surgical instrument 50 relative to the patient 60, the region of interest 62, the target trajectory axis 210, and/or the target object 130, 230.

The method of aligning the surgical instrument 50 may further comprise using different colors for displaying the augmented reality position alignment visualization 220 and/or the augmented reality angular alignment visualization 200 so that the user can distinguish the respective alignment visualizations. The different colors for the augmented reality visualizations may be selected from a base color of a trajectory by equidistant placing of alternate colors in a chromaticity space around a white point and selecting their dominant wavelength by extrapolation. For example, the colors may be selected from high-luminance complementary colors selected from the group comprising yellow, pink, green and cyan.

The method may also comprise highlighting the augmented reality position alignment visualization 220 and/or the augmented reality angular alignment visualization 200 to the user based on the distance of the surgical instrument 50 to the target trajectory axis 210. For example, the color and or the line weight of the lines representing the augmented reality position alignment visualization 220 may be different from the color and or the line weight of the lines representing the augmented reality angular alignment visualization 200. As described above, this may be utilized to allow the user to distinguish between the augmented reality position alignment visualization 220 and/or the augmented reality angular alignment visualization 200 displayed on the lens 36 of the head-mounted display 30.

The step of highlighting of the target trajectory axis 210 may further comprise the step of hiding all additional trajectories from the user except the one with the minimum distance. The step of highlighting the target trajectory axis 210 may also comprise showing all additional trajectories except the one with the minimum distance with increased transparency. For example, when the surgical instrument 50 is properly aligned with the direction and orientation corresponding to the first deviation vector 222 of the augmented reality position alignment visualization 220, the first deviation vector 222 may be hidden or displayed as transparent on the lens 36 of the head-mounted display 30. By contrast, if the surgical instrument 50 is misaligned with the direction and orientation corresponding to the first deviation vector 222 of the augmented reality position alignment visualization 220, the first deviation vector 222 may be highlighted on the lens 36 of the head-mounted display 30 to signal to the user that a correction in the alignment is needed based on the target trajectory axis 210.

The method of aligning the surgical instrument 50 may further comprise the step of displaying on the head-mounted display 30 the augmented reality position alignment visualization 220 as two axis-aligned deviation vectors 222, 224 wherein the distance between the surgical instrument 50 and the target trajectory axis 210 is computed based on the distance of the tip 54 of the surgical instrument 50 to at least one selected from the group consisting of a segment connecting the target object 130, 230 and an entry point of the target trajectory axis 210, a line connecting the target object 130, 230 and the entry point of the target trajectory axis 210, and the target object 130, 230 or the entry point of the target trajectory axis 210.

The method of aligning the surgical instrument 50 wherein the decomposition of the distance vector into two axis-aligned deviation vectors 222, 224 is relative to two eigenvectors derived from: two of the three primary patient axes with the highest angle to the target trajectory axis 210, or a line of sight axis being projected onto a plane perpendicular to the target trajectory axis 210 and attached to the closest point on the target trajectory axis 210 from the tip 54 of the surgical instrument 50, and a perpendicular vector in the same plane to the projected line of sight axis.

The method of aligning the surgical instrument 50 may further comprise the step of scaling the augmented reality position alignment visualization 220 to allow the user to more easily observe small deviations in the position and/or alignment of the surgical instrument 50 relative to the target trajectory axis 210. For example, the length of the first deviation vector 222 and/or the second deviation vector 224 may be scaled up to allow the user to more easily observe small deviations. Alternatively, the length of the first deviation vector 222 and/or the second deviation vector 224 may be scaled down to allow the augmented reality visualization to fit on the lens 36 of the head-mounted display 30. The scaling of the decomposition of the distance vector may be limited to an absolute maximum visualized length and a maximum visualized length in relation to a field of view of the head-mounted display 30.

The method of aligning the surgical instrument 50 wherein the decomposition of the deviation angle 206 is relative to two eigenvectors derived from: two of the three primary patient axes with the highest angle to the target trajectory axis, or a line of sight axis being projected onto a plane perpendicular to the target trajectory axis and attached to the closest point on the target trajectory axis from the tip 54 of the surgical instrument 50, and a perpendicular vector in the same plane to the projected line of sight axis.

The method of aligning the surgical instrument 50 wherein the visualization of the deviation angle 206 comprises: a position correct augmented reality visualization of the instrument axis 240, the target trajectory axis 210 and an arc representing the deviation angle 206 connecting proximal ends of both the first angular vector 204 representing the instrument axis 240 and the second angular vector 202 representing the target trajectory axis 210, or an axonometry of the position correct augmented reality visualization.

The method of aligning the surgical instrument 50 may further comprise the step of displaying a first augmented reality textual label 310 for describing the distance from the tip 54 of the surgical instrument 50 to the target trajectory axis 210 and a second augmented reality textual label 310 for describing the deviation angle 206 in degrees between the instrument axis 240 and the target trajectory axis 210 positioned in or near the angular visualization.

The method of aligning the surgical instrument 50 may further comprise the step of displaying an augmented reality visualization of the target object 130, 230 to be placed or removed at a target point of the target trajectory axis 210.

The method of aligning the surgical instrument 50 may further comprise the step of displaying the augmented reality visualization of the target object 130, 230 to be placed or removed at a target point of the target trajectory axis 210 wherein the augmented reality visualization of the target object 130, 230 is positioned at the target position or at the current position of the surgical instrument 50.

The method of aligning the surgical instrument 50 may further comprise the step of displaying an augmented reality visualization of a slice of patient image data. This step may comprise selecting an augmented reality visualization location chosen by the user to be one of a fixed frame in space, a floating frame 300 following head movement, an in-place at the position of the patient image data slice, or an offset from the patient position by a user defined fixed spatial vector. The user may manipulate the slice of the patient image data using control buttons 320, 322, 324, 326, 328 displayed on the lens 36 of the head-mounted display 30. The user may select the control buttons 320, 322, 324, 326, 328 displayed on the lens 36 using hand and/or facial gestures. This step may further comprise color mapping from patient image data color information to augmented reality visualization color information including alpha transparency target ranges. The step may further comprise a user interaction by which the user can use any of voice, mouse, keyboard, gaze, or surgical instruments to choose and reposition the augmented reality visualization location and select the slice of patient image data.

The method of aligning the surgical instrument 50 may further comprise displaying a region of interest indicator. The region of interest indicator may comprise an augmented reality textual label 310 shown in the vicinity of the region of interest 62 or an augmented reality boundary visualization demarcating the region of interest 62. The region of interest indicator may further comprise a color mapping method which highlights to the user the augmented reality textual labels 310 and augmented reality boundary visualization based on the distance of the surgical instrument 50 to the region of interest 62.

Several configurations of augmented reality visualizations, such as the augmented reality position alignment visualization 220 and/or the augmented reality angular alignment visualization 200, are described above. While many of the configurations of the augmented reality visualization are described with regard to being displayed on a lens 36 of a head-mounted display 30 and/or on the head-mounted display 30, it should be understood that it is also contemplated that any of the various configurations of the augmented reality visualizations may also be display on a display 22. The display 22 may comprise a cathode ray tube display (CRT), light-emitting diode display (LED), electroluminescent display (ELD), liquid crystal display (LCD), organic light-emitting diode display (OLED), digital light processing display (DLP), projection monitor, or similar device.

Several configurations of a surgical navigation system 20 and/or an augmented reality visualization have been discussed in the foregoing description. However, the configurations discussed herein are not intended to be exhaustive or limit the disclosure to any particular form. The terminology which has been used is intended to be in the nature of words of description rather than of limitation. Many modifications and variations are possible in light of the above teachings and the disclosure may be practiced otherwise than as specifically described.

CLAUSES FOR ADDITIONAL CONFIGURATIONS (ORIGINAL EP CLAIMS)

I. A guidance system for the alignment of a surgical instrument comprising a stereoscopic head-mounted display comprising at least a HMD tracker, a surgical navigation system with tracking system, patient data registered to a patient tracker trackable by the tracking system, a planning system for planning one or more trajectories on the patient data, a navigated instrument tracked by the tracking system, a AR position alignment visualization, an AR angular alignment visualization.

I-a. The guidance system of clause I may be configured to display two axis-aligned deviation vectors for the position alignment visualization which are the decomposition of the distance vector from the nearest point on the trajectory axis of the tip of the navigated instrument to the tip of the navigated instrument and which are scaled in length by a scaling function to allow the user to see small deviations on the stereoscopic head-mounted display.

I-b. The guidance system of clause I or I-a may further be configured to display the angular alignment visualization consisting of one or two deviation angles which show the angle between the direction vector of the axis of the instrument and the direction vector of the trajectory axis or the decomposition of said angle into two deviation angles and each of which might are scaled in opening angle by a scaling function to allow the user to see small deviations.

I-c. The guidance system of any of clauses I, I-a, and I-b may further be configured to update the visualizations continuously based on the tracking system to show the relative location of the navigated instrument to the patient data from the perspectives of the both eyes of the stereoscopic head-mounted display.

I-d. The guidance system of any of clauses I, I-a, I-b, and I-c may further be configured to use different colors for the visualizations so that the user can distinguish the respective alignment visualizations and to highlight the visualizations to the user based on the distance of the navigated instrument to each trajectory.

II. A method for the alignment of a surgical instrument using a guidance system of clause I, the method comprising the steps of: updating the visualizations continuously based on the tracking system to show the relative location of the navigated instrument to the patient data from the perspectives of the both eyes of the stereoscopic HMD; using different colors for the visualizations so that the user can distinguish the respective alignment visualizations; and highlighting the visualizations to the user based on the distance of the navigated instrument to each trajectory.

II-a. The method according to clause II may further comprise using and/or displaying two axis-aligned deviation vectors for the position alignment visualization which are the decomposition of the distance vector from the nearest point on the trajectory axis of the tip of the navigated instrument to the tip of the navigated instrument and which are scaled in length by a scaling function to allow the user to see small deviations.

II-b. The method according to clauses II or II-a may further comprise using and/or displaying the angular alignment visualization consisting of one or two deviation angles which show the angle between the direction vector of the axis of the instrument and the direction vector of the trajectory axis or the decomposition of said angle into two deviation angles and each of which might are scaled in opening angle by a scaling function to allow the user to see small deviations.

II-c. The method according to any of clauses II, II-a, and II-b, characterized in that the distance between the navigated instrument and the trajectory is computed based on the distance of either the tip of the navigated instrument to at least one selected from the group consisting of the segment connecting target and entry point of the trajectory, the line connecting target and entry point of the trajectory, and target or entry point of the trajectory.

II-d. The method according to any of clauses II, II-a, and II-b, characterized in that the angular deviation between the navigated instrument and the trajectory is computed based on the angle between the normal of the axis of the navigated instrument and the normal of the line connecting target and entry point of the trajectory.

II-e. The method according to any of clauses II, II-a, and II-b, characterized in that the highlighting of trajectories hides all trajectories from the user except the one with the minimum distance and shows all trajectories except the one with the minimum distance with increased transparency.

II-f. The method according to any of clauses II, II-a, and II-b, characterized in that the decomposition of the distance vector in two axis-aligned deviation vectors is relative to the two eigenvectors derived from: the two of the three primary patient axes with the highest angle to the trajectory axis, or the line of sight axis being projected onto the plane perpendicular to the trajectory axis and attached to the closest point on the trajectory axis from the tip of the navigated instrument, and the perpendicular vector in the same plane to the projected line of sight axis.

II-g. The method according to any of clauses II, II-a, and II-b, characterized in that the scaling of the decomposition of the distance vector is limited to an absolute maximum visualized length and a maximum visualized length in relation to the field of view of the head-mounted display.

II-h. The method according to any of clauses II, II-a, and II-b, characterized in that the decomposition of the two deviation angles is relative to the two eigenvectors derived from: the two of the three primary patient axes with the highest angle to the trajectory axis, or the line of sight axis being projected onto the plane perpendicular to the trajectory axis and attached to the 5 closest point on the trajectory axis from the tip of the navigated instrument, and the perpendicular vector in the same plane to the projected line of sight axis.

II-i. The method according to any of clauses II, II-a, and II-b, characterized in that the visualization of a deviation angle consists of: a position correct augmented reality visualization of the current normal axis, the target normal axis and the arc connecting the proximal ends of both current and target normal axis, or an axonometry of the position correct augmented reality visualization.

II-j. The method according to any of clauses II, II-a, and II-b, further using an AR textual label for describing the distance from the instrument tip to the trajectory target and an AR textual label for describing the angular deviation in degrees between the instrument axis and the trajectory axis positioned in or near the angular visualization.

II-k. The method according to any of clauses II, II-a, and II-b, further using an AR visualization of the trajectory.

II-l. The method according to any of clauses II, II-a, and II-b, further using an AR visualization of the target object to be placed or removed at the target point of the trajectory characterized in that the AR visualization of the target object is positioned at the target position or at the current position of the navigated tool.

II-m. The method according to any of clauses II, II-a, and II-b, further comprising the step of an AR visualization of the target object to be placed or removed at the target point of the trajectory.

II-n. The method according to any of clauses II, II-a, and II-b, characterized in that the different colours for the visualization are selected from a base colour of a trajectory by equidistant placing of alternate colours in a chromaticity space around the white point and selecting their dominant wavelength by extrapolation or that the colours are selected from high-luminance complementary colours selected from the group comprising yellow, pink, green and cyan.

II-o. The method according to any of clauses II, II-a, and II-b, further comprising the step of an AR visualization of a slice of patient image data comprising the steps of: a AR visualization location chosen by the surgeon to be one of fixed frame in space, floating frame following head movement, in-place at the position of the patient image data slice or offset from the patient position by a user defined fixed spatial vector; a color mapping from patient image data color information to AR visualization color information including alpha transparency target ranges; and a user interaction by which the user can use any of voice, mouse, keyboard, gaze, or navigated surgical instruments to choose and reposition the AR visualization location and select the slice of patient image data.

II-p. The method according to any of clauses II, II-a, and II-b, further comprising the use of a region of interest indicator comprising: a AR textual labels shown in the vicinity of the region of interests or a AR boundary visualizations demarcating the region of interests, and a color mapping method which highlights to the user the AR textual labels and AR boundary visualization based on the distance of the navigated instrument to the region of interest.

CLAUSES FOR ADDITIONAL CONFIGURATIONS (ORIGINAL PCT CLAIMS)

III. A head-mounted display for use with surgical navigation system including a patient tracker and a surgical instrument tracker, the surgical navigation system configured to plan a target trajectory axis based on patient data and for the alignment of an instrument axis that is at least partially defined by a tip of a surgical instrument with the target trajectory axis, said head-mounted display comprising:
a lens; and
wherein the head-mounted display is configured to display an augmented reality position alignment visualization comprising two axis-aligned deviation vectors comprising the decomposition of a distance vector from a point on the target trajectory axis to the tip of the surgical instrument; and/or
wherein the head-mounted display is further configured to display an augmented reality angular alignment visualization comprising a deviation angle which represent the angle between a first angular vector representative of the instrument axis and a second angular vector representative of the target trajectory axis.

III-a. The head-mounted display of clause III, wherein the two axis-aligned deviation vectors are configured to be scaled in length to allow the user to see small deviations in the distance from the surgical instrument axis to the target trajectory axis.

III-b. The head-mounted display of clause III, wherein the deviation angle is configured to be scaled to allow the user to see small deviations in the angle between the first angular vector and the second angular vector.

III-c. The head-mounted display of clause III, wherein the augmented reality angular alignment visualization comprises a decomposition of the angle between a first angular vector representative of the instrument axis and a second angular vector representative of the target trajectory axis of the angle into two deviation angles.

III-d. The head-mounted display of clause III, wherein the augmented reality position alignment visualization comprises a first color and the augmented reality angular alignment visualization comprises a second color; and
wherein the first color is distinguishable from the second color.

IV. A method of aligning a surgical instrument using a surgical navigation system, the surgical navigation system including a tracking unit configured to track the position of a head-mounted display, a patient tracker, and a surgical instrument tracker coupled to a surgical instrument having a tip and defines an instrument axis, and wherein the surgical navigation system is configured to plan a target trajectory axis based on patient data registered to the patient tracker, the method comprising the steps of:
displaying on the head-mounted display an augmented reality position alignment visualization as two axis-aligned deviation vectors comprising the decomposition of a distance vector from a point on the target trajectory axis to the tip of the surgical instrument, and/or
displaying on the head-mounted display an augmented reality angular alignment visualization comprising a deviation angle which shows the angle between a first angular vector representative of the surgical instrument axis and a second angular vector representative of the target trajectory axis; and
continuously updating the augmented reality position alignment visualization and/or the augmented reality angular alignment visualization displayed on the head-mounted display based on the tracking unit to indicate the location of the surgical instrument axis relative to the target trajectory axis from the perspectives of the head-mounted display.

IV-a. The method according to clause IV, wherein the target trajectory axis defined by a line connecting a target object and an entry point.

IV-b. The method according to clauses IV or IV-a, further comprising displaying an augmented reality visualization of an instrument axis of the surgical instrument on the head-mounted display.

IV-c. The method according to clause IV, further comprising using different colors for displaying the augmented reality position alignment visualization and/or the augmented reality angular alignment visualization so that the user can distinguish the respective alignment visualization; and
highlighting the augmented reality position alignment visualization and/or the augmented reality angular alignment visualization to the user based on the distance of the surgical instrument to the target trajectory axis.

IV-d. The method according to clause IV, wherein the distance between the surgical instrument and the target trajectory axis is computed based on the distance of the tip of the surgical instrument to at least one selected from the group consisting of a segment connecting a target object and an entry point of the target trajectory axis, a line connecting the target object and the entry point of the target trajectory axis, the target object, and the entry point of the trajectory.

IV-e. The method according to clause IV-c, wherein the highlighting of the target trajectory axis comprises hiding all additional trajectories from the user except the one with the minimum distance.

IV-f. The method according to clause IV-c, showing all additional trajectories except the one with the minimum distance with increased transparency.

IV-g. The method according to clause IV, wherein the decomposition of the distance vector into two axis-aligned deviation vectors is relative to two eigenvectors derived from:

two of the three primary patient axes with the highest angle to the target trajectory axis, and a line of sight axis being projected onto a plane perpendicular to the target trajectory axis and attached to the closest point on the target trajectory axis from the tip of the surgical instrument, and a perpendicular vector in the same plane to the projected line of sight axis.

IV-h. The method according to clause IV, further comprising scaling the augmented reality position alignment visualization;

wherein the scaling of the decomposition of the distance vector is limited to an absolute maximum visualized length and a maximum visualized length in relation to a field of view of the head-mounted display.

IV-i. The method according to clause IV, wherein the decomposition of the two deviation angles is relative to two eigenvectors derived from:

two of the three primary patient axes with the highest angle to the target trajectory axis, and a line of sight axis being projected onto a plane perpendicular to the target trajectory axis and attached to the closest point on the target trajectory axis from the tip of the surgical instrument, and a perpendicular vector in the same plane to the projected line of sight axis.

IV-j. The method according to clause IV-c, wherein the visualization of the deviation angle comprises:

a position correct augmented reality visualization of the instrument axis, the target trajectory axis and an arc connecting proximal ends of both the instrument axis and the target trajectory axis.

IV-k. The method according to clause IV-c, wherein the visualization of the deviation angle comprises:

an axonometry of a position correct augmented reality visualization of the instrument axis.

IV-l. The method according to clause IV-b, further comprising displaying a first augmented reality textual label for describing the distance from the tip of the surgical instrument to the target trajectory axis and a second augmented reality textual label for describing the deviation angle in degrees between the instrument axis and the target trajectory axis positioned in or near the angular visualization.

IV-m. The method according to clause IV, further comprising displaying an augmented reality visualization of a target object to be placed or removed at a target point of the target trajectory axis wherein the augmented reality visualization of the target object is positioned at the target position or at the current position of the surgical instrument.

IV-n. The method according to clause IV, further comprising the step of an augmented reality visualization of a target object to be placed or removed at a target point of the target trajectory axis.

IV-o. The method according to clause IV-a, wherein the different colors for the augmented reality visualizations are selected from a base color of a trajectory by equidistant placing of alternate colors in a chromaticity space around a white point and selecting their dominant wavelength by extrapolation; and/or wherein the colors are selected from high-luminance complementary colors selected from the group comprising yellow, pink, green and cyan.

IV-p. The method according to clause IV, further comprising the step of displaying an augmented reality visualization of a slice of patient image data comprising the steps of:

selecting an augmented reality visualization location chosen by the surgeon to be one of a fixed frame in space, a floating frame following head movement, an in-place at the position of the patient image data slice, or an offset from the patient position by a user defined fixed spatial vector;

a color mapping from patient image data color information to augmented reality visualization color information including alpha transparency target ranges; and a user interaction by which the user can use any of voice, mouse, keyboard, gaze, or surgical instruments to choose and reposition the augmented reality visualization location and select the slice of patient image data.

IV-q. The method according to clause IV, further comprising displaying a region of interest indicator, said region of interest indicator comprising:

an augmented reality textual labels shown in the vicinity of the region of interests or an augmented reality boundary visualizations demarcating the region of interests, and a color mapping method which highlights to the user the augmented reality textual labels and augmented reality boundary visualization based on the distance of the navigated instrument to the region of interest.

V. A surgical navigation system, a patient tracker trackable by the surgical navigation system, and a surgical instrument trackable by the surgical navigation system, said surgical instrument guidance system comprising:

a display;

a controller configured to display an augmented reality position alignment visualization on the display as two axis-aligned deviation vectors comprising a decomposition of a distance vector from a target point on a target trajectory axis to the surgical instrument on said display; and/or wherein the controller is further configured to display an augmented reality angular alignment visualization on the display comprising a deviation angle which represent the angle between a first angular vector representative of the instrument axis and a second angular vector representative of the target trajectory axis.

What is claimed is:

1. A head-mounted display system for use with a surgical navigation system, a patient tracker trackable by the surgical navigation system, and a surgical instrument trackable by the surgical navigation system, said head-mounted display system comprising:

a lens; and
a controller configured to display an augmented reality position alignment visualization as two axis-aligned deviation vectors comprising a decomposition of a distance vector from a target point on a target trajectory axis to the surgical instrument on said lens.

2. The head-mounted display system of claim 1, wherein the controller is configured to generate an augmented reality angular alignment visualization on said lens.

3. The head-mounted display system of claim 2, wherein the augmented reality angular alignment visualization comprises a deviation angle which represent an angle between a first angular vector representative of the instrument axis and a second angular vector representative of the target trajectory axis, the length of a first line and a second line representing the deviation angle is configured to be scaled to allow the user to see small deviations.

4. The head-mounted display system of claim 2, wherein the augmented reality angular alignment visualization comprises a decomposition of an angle between a first angular vector representative of the instrument axis and a second angular vector representative of the target trajectory axis of the angle into two deviation angles, the length of lines representing the two deviation angles are configured to be scaled to allow the user to see small deviations.

5. The head-mounted display system of claim 2, wherein the augmented reality position alignment visualization comprises a first color and the augmented reality angular alignment visualization comprises a different color that is distinguishable from the first color.

6. The head-mounted display system of claim 1, wherein the controller is configured to scale the two axis-aligned deviation vectors displayed on said lens.

7. The head-mounted display system of claim 2, wherein the augmented reality angular alignment visualization comprises a deviation angle which represents the angle between a first angular vector representative of an axis parallel to the instrument axis and a second angular vector representative of the target trajectory axis.

8. A surgical navigation system comprising:
a head-mounted display comprising a lens;
a surgical navigation system comprising a tracking unit;
a patient tracker registered to patient data and trackable by said surgical navigation system;
a surgical instrument having an instrument tracker trackable by said surgical navigation system, said instrument defines an instrument axis; and
a controller configured to generate an augmented reality position alignment visualization as two axis-aligned deviation vectors comprising a decomposition of a distance vector from a target point on a target trajectory axis to a point on the surgical instrument to display on said lens of said head-mounted display.

9. The surgical navigation system of claim 8, wherein the controller is configured to scale the two axis-aligned deviation vectors displayed on said lens.

10. The surgical navigation system of claim 8, wherein the controller is configured to generate an augmented reality angular alignment visualization to display on the lens.

11. The surgical navigation system of claim 10, wherein the augmented reality angular alignment visualization comprises a deviation angle which represents the angle between a first angular vector representative of an axis parallel to the instrument axis and a second angular vector representative of the target trajectory axis.

12. The surgical navigation system of claim 11, wherein the controller is configured to scale a length of a first line and a second line representing the deviation angle to allow the user to see small deviations in the deviation angle.

13. The surgical navigation system of claim 10, wherein the augmented reality angular alignment visualization comprises a decomposition of an angle between a first angular vector representative of the instrument axis and a second angular vector representative of the target trajectory axis into two deviation angles.

14. A method of displaying surgical navigation information using a head-mounted display system including a surgical navigation system and a surgical instrument having a tip and at least partially defining an instrument axis in view of a surgical plan including a target trajectory axis, said method comprising:
displaying an augmented reality position alignment visualization comprising two axis-aligned deviation vectors on a head-mounted display, said two-axis aligned deviation vectors comprising a first deviation vector and a second deviation vector wherein the first deviation vector and second deviation vector are representative of a decomposition of a distance vector from a point on the target trajectory axis to the tip of the surgical instrument; and
updating the augmented reality position alignment visualization displayed on the head-mounted display to indicate a relative location of the surgical instrument to the target trajectory axis from the perspective of the head-mounted display.

15. The method according to claim 14, wherein the decomposition of the distance vector into two axis-aligned deviation vectors is relative to two eigenvectors derived from:
two of the three primary patient axes derived from the orientation of the patient with the highest angle to the target trajectory axis.

16. The method according to claim 14, wherein the decomposition of the distance vector into two axis-aligned deviation vectors is relative to two eigenvectors derived from:
a line of sight axis being projected onto a plane perpendicular to the target trajectory axis and attached to the closest point on the target trajectory axis from the tip of the surgical instrument, and a perpendicular vector in the same plane to the projected line of sight axis.

17. The method according to claim 14, further comprising displaying an augmented reality angular alignment visualization comprising a deviation angle which shows the angle between a first angular vector representative of the axis of the surgical instrument and a second angular vector representative of the target trajectory axis.

18. The method according to claim 17, further comprising updating the augmented reality angular alignment to indicate an angle of an axis of the surgical instrument relative to the target trajectory axis from the perspective of the head-mounted display.

19. The method according to claim 17, further comprising using a first color for displaying the augmented reality position alignment visualization or the augmented reality angular alignment visualization and using a different color for the other of the augmented reality position alignment visualization or the augmented reality angular alignment visualization.

20. The method according to claim 17, further comprising highlighting the augmented reality position alignment visualization and/or the augmented reality angular alignment visualization to the user based on the distance of the surgical instrument to the target trajectory axis.

21. The method according to claim 14, wherein the distance between the surgical instrument and the target trajectory axis is computed based on the distance of the tip of the surgical instrument to at least one basis selected from the group consisting of a segment connecting a target object and an entry point of the target trajectory axis, a line connecting the target object and the entry point of the target trajectory axis, and the target object or the entry point of the trajectory.

* * * * *